US009975975B2

(12) United States Patent
Ewart et al.

(10) Patent No.: US 9,975,975 B2
(45) Date of Patent: May 22, 2018

(54) BIS-BIPHENYLPHENOXY CATALYSTS FOR POLYMERIZATION OF LOW MOLECULAR WEIGHT ETHYLENE-BASED POLYMERS

(71) Applicant: Dow Global Technologies LLC, Midland, MI (US)

(72) Inventors: Sean W. Ewart, Pearland, TX (US); Richard J. Keaton, Pearland, TX (US); Jerzy Klosin, Midland, MI (US); Ruth Figueroa, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days. days.

(21) Appl. No.: 15/310,553

(22) PCT Filed: Jul. 23, 2015

(86) PCT No.: PCT/US2015/041664
§ 371 (c)(1),
(2) Date: Nov. 11, 2016

(87) PCT Pub. No.: WO2016/014749
PCT Pub. Date: Jan. 28, 2016

(65) Prior Publication Data
US 2017/0137550 A1 May 18, 2017

Related U.S. Application Data

(60) Provisional application No. 62/028,637, filed on Jul. 24, 2014.

(51) Int. Cl.
C08F 4/653 (2006.01)
C08F 4/6592 (2006.01)
C08F 10/00 (2006.01)
C08F 210/16 (2006.01)
C08F 4/659 (2006.01)

(52) U.S. Cl.
CPC ........ *C08F 210/16* (2013.01); *C08F 4/65904* (2013.01); *C08F 4/65925* (2013.01); *C08F 4/65927* (2013.01); *C08F 10/00* (2013.01)

(58) Field of Classification Search
CPC ..... C08F 4/64103; C08F 10/02; C08F 210/16
See application file for complete search history.

(56) References Cited

U.S. PATENT DOCUMENTS

| 5,189,192 | A | 2/1993 | LaPointe et al. |
| 5,453,410 | A | 9/1995 | Kolthammer et al. |
| 6,806,326 | B2 | 10/2004 | Stevens et al. |
| 6,869,904 | B2 | 3/2005 | Boussie et al. |
| 7,060,848 | B2 | 6/2006 | Boussie et al. |
| 9,605,098 | B2 * | 3/2017 | Klosin |
| 2011/0282018 | A1 | 11/2011 | Klosin et al. |
| 2013/0079483 | A1 | 3/2013 | Robert et al. |
| 2014/0121342 | A1 | 5/2014 | Diamond et al. |
| 2015/0148490 | A1 | 5/2015 | Kapur et al. |

FOREIGN PATENT DOCUMENTS

| WO | 2007/136494 A2 | 11/2007 |
| WO | WO2014/210333 | * 12/2014 |

OTHER PUBLICATIONS

PCT/US2015/041664, International Search Report and Written Opinion dated Oct. 12, 2015.
PCT/US2015/041664, International Preliminary Report on Patentability dated Jan. 24, 2017.

* cited by examiner

Primary Examiner — Caixia Lu

(57) ABSTRACT

The invention provides a process, and transition metal complex, to form an ethylene-based polymer, said process comprising polymerizing ethylene, and optionally at least one comonomer, in the presence of at least one molecular transition metal complex selected from Formula 1, as described herein.

13 Claims, No Drawings

BIS-BIPHENYLPHENOXY CATALYSTS FOR POLYMERIZATION OF LOW MOLECULAR WEIGHT ETHYLENE-BASED POLYMERS

REFERENCE TO RELATED APPLICATIONS

The present application claims the benefit of U.S. Provisional Application No. 62/028,637, filed Jul. 24, 2014, and incorporated herein by reference.

BACKGROUND

Low molecular weight ethylene-based polymers are used in formulations to make hot melt adhesives, and other types of adhesives. Many such polymers are produced with a constrained geometry type catalyst system at low temperatures (<135° C.). It is desirable to find new polymerizations and catalyst systems capable of making these low molecular weight polymers at elevated temperatures, to allow for increased reactor throughput, decreased heat input for solvent devolatilization, and decreased reactor fouling. With such high temperature polymerizations and catalysts systems, it is desirable to use equivalent or lower levels of hydrogen, as compared to the current incumbent constrained geometry catalyst systems, to reduce or prevent gas-out from occurring in either the reactor, the reactor feeds, or the post reactor heater(s).

Some conventional polymerizations and catalysts systems are described in the following references: WO 2007/136494, US 2011/0282018, U.S. Pat. No. 6,869,904, U.S. Pat. No. 7,060,848, U.S. Pat. No. 6,806,326, U.S. Pat. No. 5,453,410, and U.S. Pat. No. 5,189,192. However, the polymerization of ethylene, and the polymerization of ethylene with one or more alpha-olefins, by transition metal catalysts of the art, are generally known to produce relatively high molecular weight homopolymers and copolymers, at high polymerization temperatures and low levels of hydrogen. Frequently such polymers and copolymers exhibit molecular weights (e.g., Mw) greater than 100,000 g/mole, and in some embodiments greater than 500,000 g/mole. At these molecular weight levels, the rheological behavior of the polymer is undesirable, because the polymers do not flow as desired, and may crystallize from the polymerization solution. As discussed, there remains a need for new polymerizations and catalyst systems, capable of making low molecular weight homopolymers and copolymers at elevated temperatures, and low hydrogen levels. This need has been met by the following invention.

SUMMARY OF THE INVENTION

The invention provides a process to form an ethylene-based polymer, said process comprising polymerizing ethylene, and optionally at least one comonomer, in the presence of at least one molecular transition metal complex selected from Formula 1:

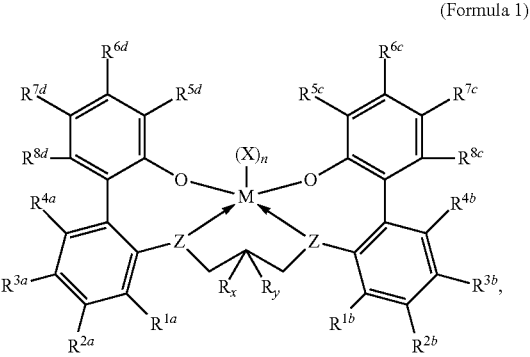

(Formula 1)

wherein M is titanium, zirconium, or hafnium, each independently being in a formal oxidation state of +2, +3, or +4;

n is an integer of from 0 to 3, wherein when n is 0, X is absent;

each X is independently a monodentate ligand that is neutral, monoanionic, or dianionic, or two X are taken together to form a bidentate ligand that is neutral, monoanionic, or dianionic;

X and n are selected such that the metal-ligand complex is neutral;

each Z moiety is, independently, —O—, —S—, —N[($C_1$-$C_{40}$)hydrocarbyl]-, or —P[($C_1$-$C_{40}$)hydrocarbyl]-;

$R_x$ is selected from the following: a substituted or unsubstituted ($C_1$-$C_{40}$)hydrocarbyl; a substituted or unsubstituted ($C_1$-$C_{40}$)heterohydrocarbyl; —Si($R^C$)$_3$, —OSi($R^C$)$_3$, —Ge($R^C$)$_3$, —P($R^C$)$_2$, —N($R^C$)$_2$, —$OR^C$, —$SR^C$, —$NO_2$, —CN, —$CF_3$, —$OCF_3$, —S(O)$R^C$, —S(O)$_2R^C$, —N=C($R^C$)$_2$, —OC(O)$R^C$, —C(O)O$R^C$, —N(R)C(O)$R^C$, —C(O)N($R^C$)$_2$, a halogen, or a hydrogen; and wherein each $R^C$ is independently a substituted or unsubstituted ($C_1$-$C_{30}$)hydrocarbyl, or a substituted or unsubstituted ($C_1$-$C_{30}$) heterohydrocarbyl;

$R_y$ is selected from the following: a substituted or unsubstituted ($C_1$-$C_{40}$)hydrocarbyl; a substituted or unsubstituted ($C_1$-$C_{40}$)heterohydrocarbyl; —Si($R^C$)$_3$, —OSi($R^C$)$_3$, —Ge($R^C$)$_3$, —P($R^C$)$_2$, —N($R^C$)$_2$, —$OR^C$, —$SR^C$, —$NO_2$, —CN, —$CF_3$, —$OCF_3$, —S(O)$R^C$, —S(O)$_2R^C$, —N=C($R^C$)$_2$, —OC(O)$R^C$, —C(O)O$R^C$, —N(R)C(O)$R^C$, —C(O)N($R^C$)$_2$, a halogen, or a hydrogen; and wherein each $R^C$ is independently a substituted or unsubstituted ($C_1$-$C_{30}$)hydrocarbyl, or a substituted or unsubstituted ($C_1$-$C_{30}$) heterohydrocarbyl; and wherein, when Rx is hydrogen, Ry is not hydrogen, and when Ry is hydrogen, Rx is not hydrogen; and wherein Rx and Ry may optionally form a ring structure; and wherein $R^{1a}$, $R^{2a}$, $R^{3a}$, $R^{4a}$, $R^{1b}$, $R^{2b}$, $R^{3b}$, $R^{4b}$, $R^{5c}$, $R^{6c}$, $R^{7c}$, $R^{8c}$, $R^{5d}$, $R^{6d}$, $R^{7d}$ and $R^{8d}$ are each, independently, selected from the following: a substituted or unsubstituted ($C_1$-$C_{40}$)-hydrocarbyl, a substituted or unsubstituted ($C_1$-$C_{40}$)heterohydrocarbyl, —Si($R^C$)$_3$, —OSi($R^C$)$_3$, —Ge($R^C$)$_3$, —P($R^C$)$_2$, —N($R^C$)$_2$, —$OR^C$, —$SR^C$, —$NO_2$, —CN, —$CF_3$, —$OCF_3$, —S(O)$R^C$, —S(O)$_2R^C$, —N=C($R^C$)$_2$, —OC(O)$R^C$, —C(O)O$R^C$, —N(R)C(O)$R^C$, —C(O)N($R^C$)$_2$, a halogen, or a hydrogen; and wherein each $R^C$ is independently a substituted or unsubstituted ($C_1$-$C_{30}$)hydrocarbyl, or a substituted or unsubstituted ($C_1$-$C_{30}$) heterohydrocarbyl; and wherein, for Formula 1, one or more hydrogen atoms may optionally be substituted with deuterium, and wherein, for Formula 1, two or more of $R^{1a}$, $R^{2a}$, $R^{3a}$, $R^{4a}$, $R^{1b}$, $R^{2b}$, $R^{3b}$, $R^{4b}$, $R^{5c}$, $R^{6c}$, $R^{7c}$, $R^{8c}$, $R^{5d}$, $R^{6d}$, $R^{7d}$ and $R^{8d}$ may optionally form one or more ring structures.

The invention also provides a transition metal complex of Formula 1.

DETAILED DESCRIPTION OF THE EMBODIMENTS

A group of novel bis-biphenyl-phenoxy based transition metal complexes have been discovered, which can operate at high polymerization temperatures (for example, ≥170° C.) and low levels of hydrogen, for the production of low molecular weight ethylene-based polymers with melt viscosities ≤50,000 cP (at 177° C.). Preferably, such polymers also have low densities (≤0.90 g/cc). By addition of a single alkyl group to the central carbon of a C3 bridged transition metal based bis-biphenyl-phenoxy catalyst, the molecular weight of the polymer product can be drastically decreased, without diminishing comonomer incorporation capability or high temperature performance. The inventive process surprisingly offers the advantage of greatly reducing molecular weight of a given ethylene-based polymer, without otherwise significantly modifying the nature of the homopolymerization or copolymerization. This molecular weight reduction, in turn, may offer a significant increase in flow behavior, which correspondingly may increase the number and types of applications for use of these products.

As discussed above, the invention provides a process to form an ethylene-based polymer, said process comprising polymerizing ethylene, and optionally at least one comonomer, in the presence of at least one molecular transition metal complex selected from Formula 1:

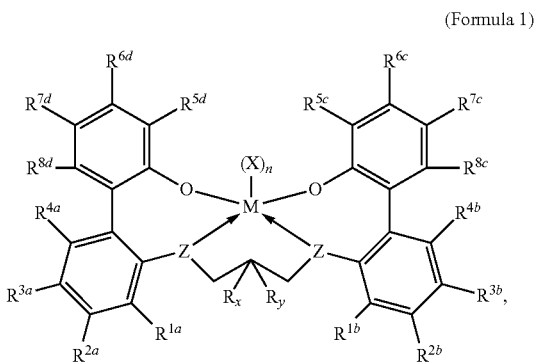

(Formula 1)

wherein Formula 1, M, n, each X, each Z, Rx, Ry, and $R^{1a}$, $R^{2a}$, $R^{3a}$, $R^{4a}$, $R^{1b}$, $R^{2b}$, $R^{3b}$, $R^{4b}$, $R^{5c}$, $R^{6c}$, $R^{7c}$, $R^{8c}$, $R^{5d}$, $R^{6d}$, $R^{7d}$ and $R^{8d}$ are described above.

The invention also provides a transition metal complex of Formula 1, as described above.

An inventive process may comprise a combination of two or more embodiments described herein.

The molecular transition metal complex of Formula 1 may comprise a combination of two or more embodiments described herein.

The following embodiments apply to the inventive processes and transition metal complexes described above.

As used herein, $R^{1a}$=R1a, $R^{1b}$=R1b, $R^{5c}$=R5c, $R^{5d}$=R5d, and so forth. As used herein, $R_x$=Rx, and $R_y$=Ry.

In one embodiment, at least one of $R^{3a}$ or $R^{3b}$ is a halogen, and further both $R^{3a}$ and $R^{3b}$ are each independently a halogen, and further fluorine, chlorine, or iodine.

In one embodiment, at least one of $R^{3a}$ or $R^{3b}$ is hydrogen or a C1-C10 alkyl, and further hydrogen or a C1-C5 alkyl.

In one embodiment, at least one of $R^{3a}$ or $R^{3b}$ is hydrogen.

In one embodiment, Rx or Ry is hydrogen, and the other is a substituted or unsubstituted (C1-C40) hydrocarbyl, and further an unsubstituted (C1-C40) hydrocarbyl.

In one embodiment, Rx or Ry is hydrogen, and the other is an unsubstituted (C1-C20) hydrocarbyl, and further an unsubstituted (C1-C10) hydrocarbyl.

In one embodiment, each Z is —O—.

In one embodiment, n is 2, and each X is independently an alkyl. In a further embodiment, each X is independently a (C1-C7)alkyl, further a (C1-C5)alkyl, further a (C1-C3) alkyl, and further each X is methyl.

In one embodiment, $R^{5c}$ and $R^{5d}$ are each independently selected from the following: 1,2,3,4-tetrahydronaphthyl; anthracenyl; 1,2,3,4-tetrahydroanthracenyl; 1,2,3,4,5,6,7,8-octahydroanthracenyl; phenanthrenyl; 1,2,3,4,5,6,7,8-octahydrophenanthrenyl; 2,6-dimethylphenyl; 2,6-diisopropylphenyl; 3,5-di(tertiary-butyl)phenyl; 3,5-diphenylphenyl; 1-naphthyl; 2-methyl-1-naphthyl; 2-naphthyl; 1,2,3,4-tetrahydronaphth-5-yl; 1,2,3,4-tetrahydronaphth-6-yl; anthracen-9-yl; 1,2,3,4-tetrahydro-anthracen-9-yl; 1,2,3,4,5,6,7,8-octahydroanthracen-9-yl; 1,2,3,4,5,6,7,8-octahydrophenanthren-9-yl; indolyl; indolinyl; quinolinyl; 1,2,3,4-tetrahydroquinolinyl; isoquinolinyl; 1,2,3,4-tetrahydro-isoquinolinyl; carbazolyl; 1,2,3,4-tetrahydrocarbazolyl; 1,2,3,4,5,6,7,8-octahydrocarbazolyl; 3,6-di(tertiary-butyl)-carbazol-9-yl; 3,6-di(tertiary-octyl)-carbazol-9-yl; 3,6-diphenylcarbazol-9-yl; 3,6-bis(2,4,6-trimethylphenyl)-carbazol-9-yl; 2,7-di(tertiary-butyl)-carbazol-9-yl; 2,7-di(tertiary-octyl)-carbazol-9-yl; 2,7-diphenylcarbazol-9-yl; or 2,7-bis(2,4,6-trimethylphenyl)-carbazol-9-yl.

In one embodiment, $R^{7c}$ and $R^{7d}$ are each independently an alkyl, further a (C1-C20)alkyl, and further a (C1-C10) alkyl.

In one embodiment, $R^{1a}$, $R^{2a}$, $R^{4a}$, $R^{1b}$, $R^{2b}$, $R^{4b}$, $R^{6c}$, $R^{8c}$, $R^{6d}$ and $R^{8d}$ are each hydrogen.

In one embodiment, Formula 1 does not contain a deuterium atom.

In one embodiment, two or more of $R^{1a}$, $R^{2a}$, $R^{3a}$, $R^{4a}$, $R^{1b}$, $R^{2b}$, $R^{3b}$, $R^{4b}$, $R^{5c}$, $R^{6c}$, $R^{7c}$, $R^{8c}$, $R^{5d}$, $R^{6d}$, $R^{7d}$ and $R^{8d}$ do not form one or more ring structures.

In one embodiment, Formula 1 is selected from the following structures a) through dd):

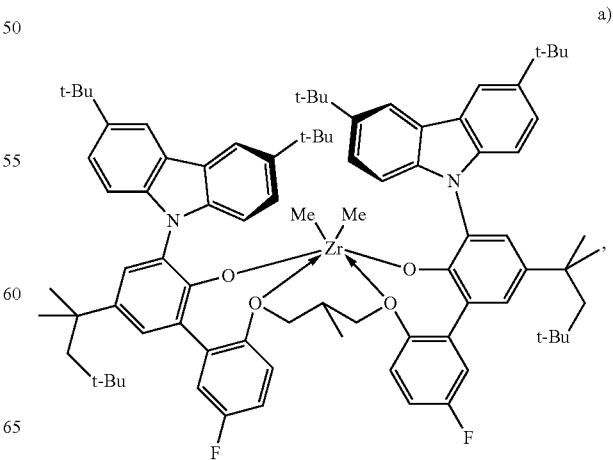

a)

b)
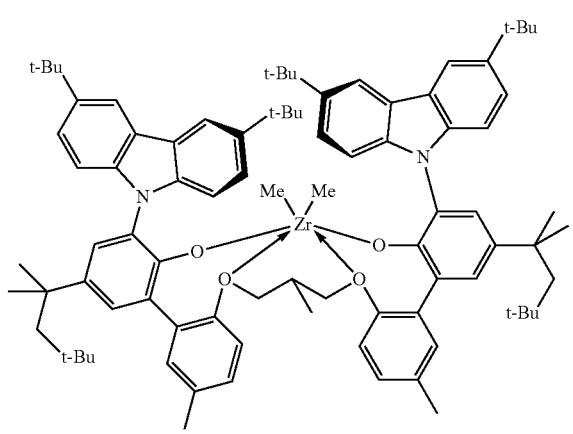
c)
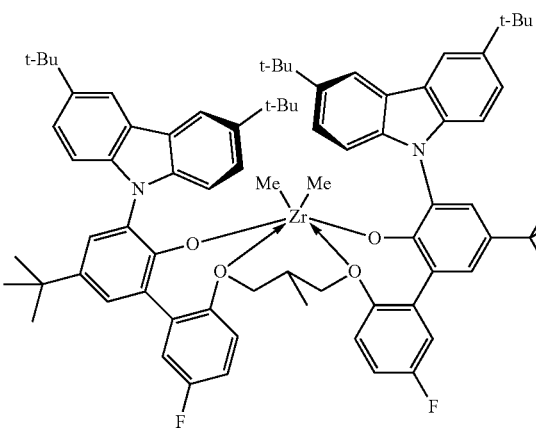
d)
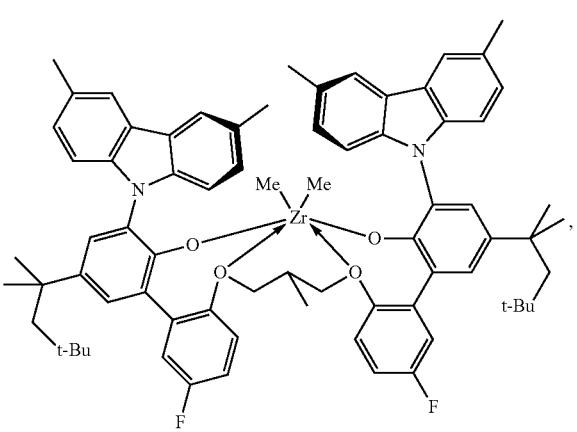
e)
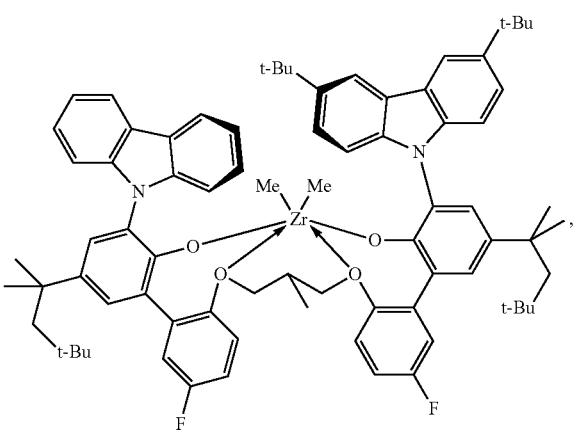
f)
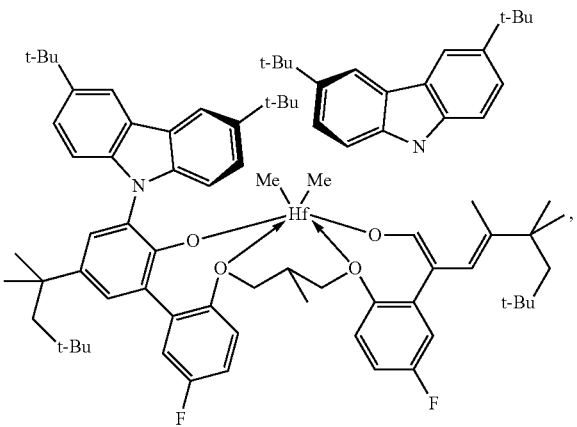
g)
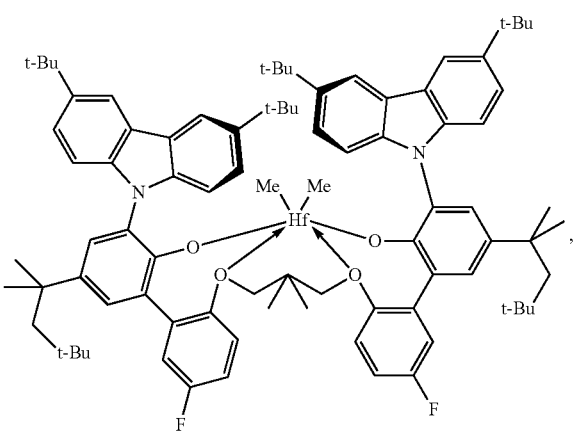

h)

i)

j)

k)

l)

m)

n)
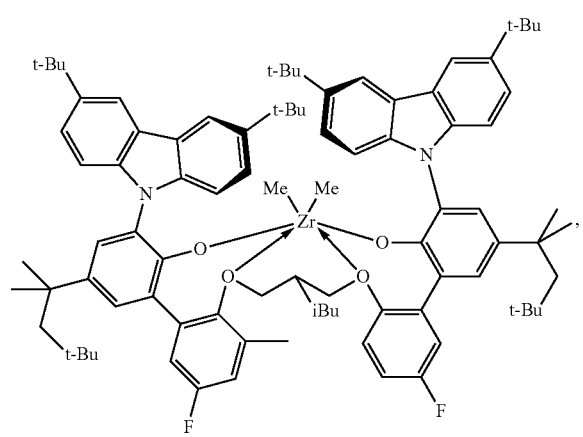
q)
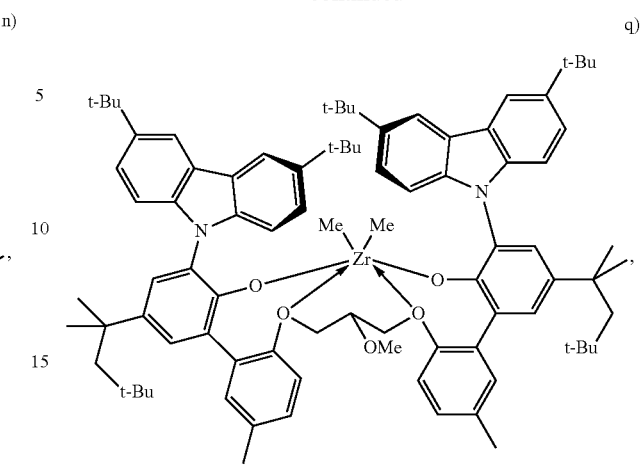
o)
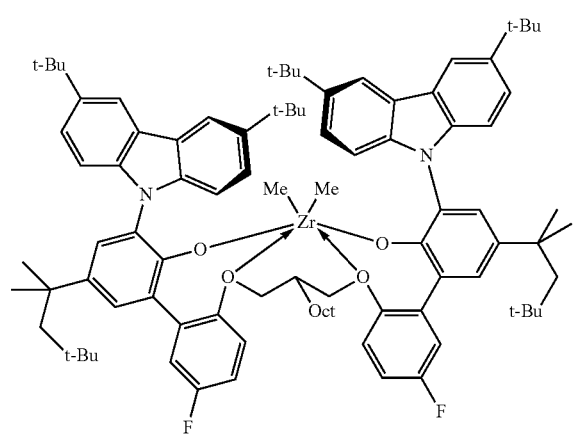
r)
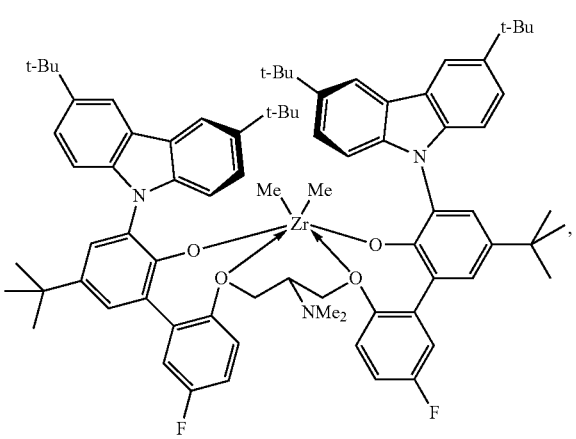
p)
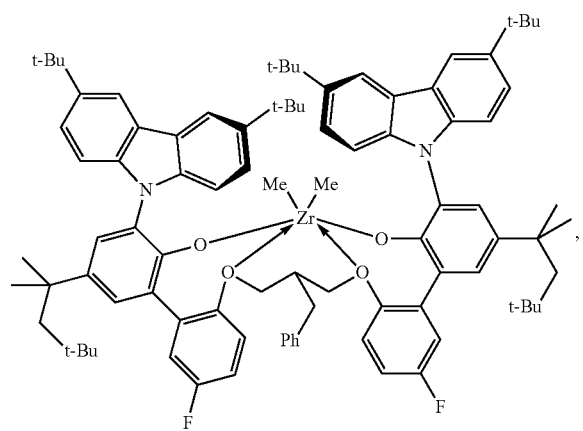
s)
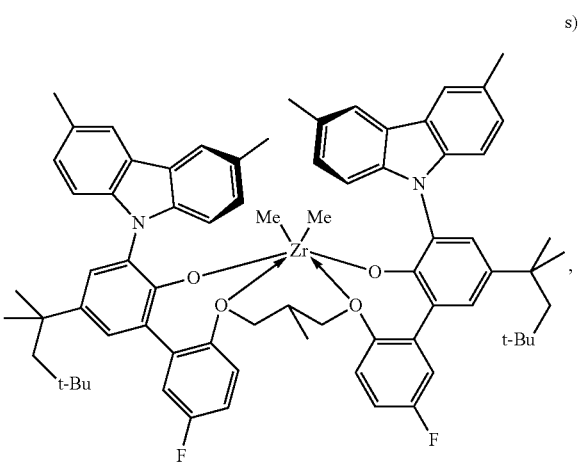

t)
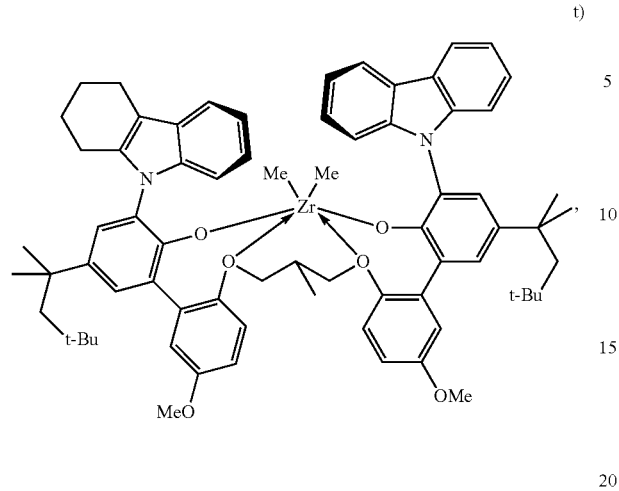
w)
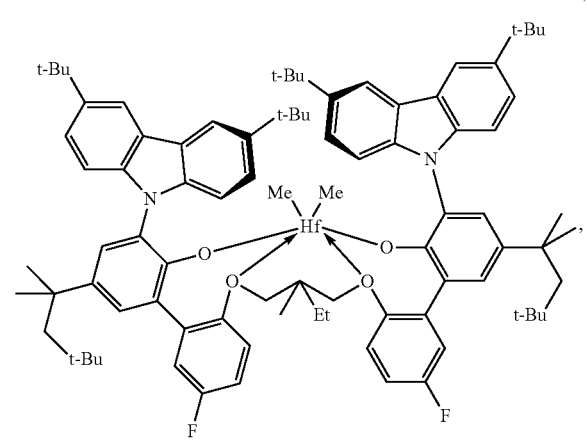
u)
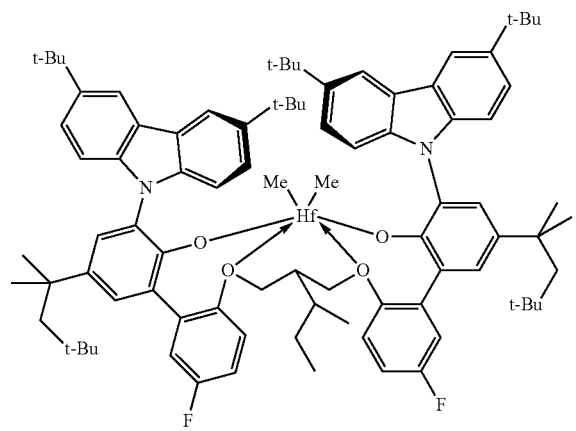
x)
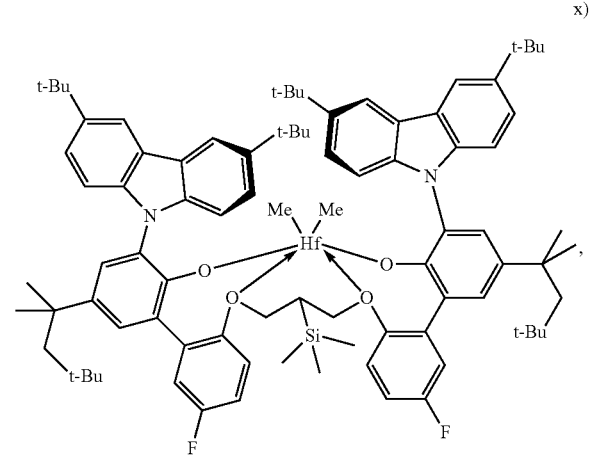
v)
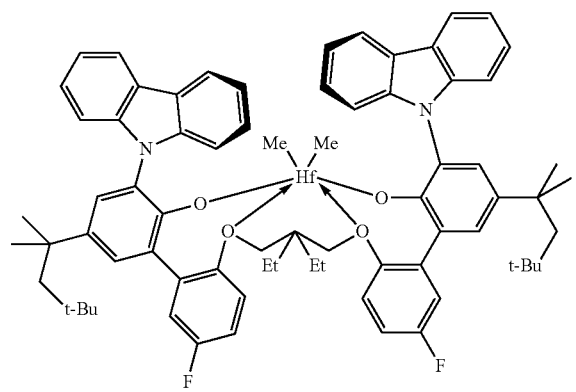
y)
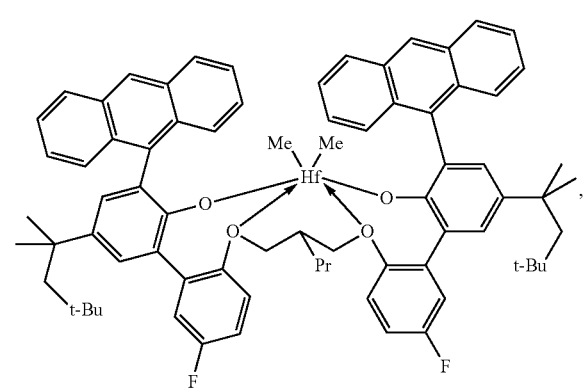

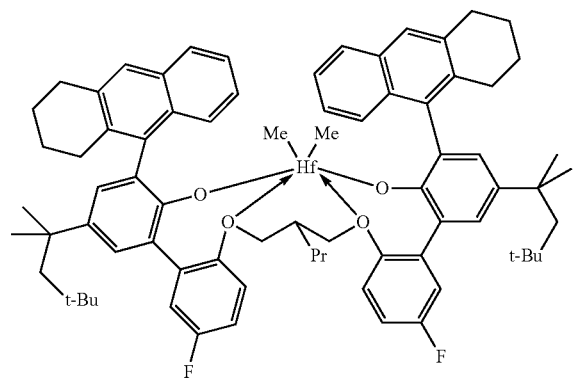
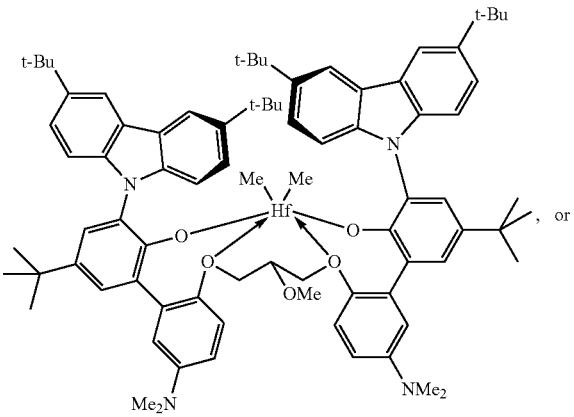

In one embodiment, Formula 1 is selected from the following structures a), b) c), j), k), l), m), n), o), p), q), r), s), t), u), y), z), aa), bb), cc) or dd); each as shown above.

In one embodiment, Formula 1 is selected from the following structures a), b) c), j), k), l), m), n), o), z), aa), bb), cc) or dd); each as shown above.

In one embodiment, Formula 1 is selected from the following structures a), b) c), j), k) or l); each as shown above.

In one embodiment, Formula 1 is selected from the following structures a), b) or c); each as shown above.

In one embodiment, the inventive process is run at a polymerization temperature from 50 to 250° C., further from 100 to 230° C., further from 150 to 200° C., further from 170 to 200° C.

In one embodiment, the inventive process is run at a polymerization temperature greater than, or equal to, 150° C., further greater than, or equal to, 160° C., further greater than, or equal to, 170° C., further greater than, or equal to, 180° C.

In one embodiment, the inventive process is run at a polymerization temperature less than, or equal to, 250° C., further less than, or equal to, 240° C., further less than, or equal to, 230° C., further less than, or equal to, 220° C.

In one embodiment, the inventive process is run in a solution polymerization, and further a continuous solution polymerization.

In one embodiment, the inventive process is run, using from 2.0 to 3.0 kg/hr ethylene, and less than, or equal to, 100 ml/min, further less than, or equal to, 90 ml/min, further less than, or equal to, 80 ml/min, hydrogen.

In one embodiment, the inventive process is run, using from 2.0 to 3.0 kg/hr ethylene, and less than, or equal to, 70 ml/min, further less than, or equal to, 60 ml/min, further less than, or equal to, 50 ml/min, hydrogen.

In one embodiment, the inventive process is run using a hydrogen ($H_2$) to ethylene (C2) ratio less than, or equal to, 2.40 liter H2 per kg C2; or less than, or equal to, 2.30 liter H2 per kg C2; or less than, or equal to, 2.20 liter H2 per kg C2. In a further embodiment, the inventive process is run at a polymerization temperature greater than, or equal to, 150° C.; or greater than, or equal to, 160° C.; or greater than, or equal to, 170° C.; or greater than, or equal to, 180° C. In a further embodiment, the inventive process is run at a polymerization temperature less than, or equal to, 250° C.; or less than, or equal to, 240° C.; or less than, or equal to, 230° C.; or less than, or equal to, 220° C.

In one embodiment, the inventive process is run using a hydrogen ($H_2$) to ethylene (C2) ratio from 0.20 to 2.40 liter H2 per kg C2; or from 0.20 to 2.30 liter H2 per kg C2; or from 0.20 to 2.20 liter H2 per kg C2. In a further embodiment, the inventive process is run at a polymerization temperature greater than, or equal to, 150° C.; or greater than, or equal to, 160° C.; or greater than, or equal to, 170° C.; or greater than, or equal to, 180° C. In a further embodiment, the inventive process is run at a polymerization temperature less than, or equal to, 250° C.; or less than, or equal to, 240° C.; or less than, or equal to, 230° C.; or less than, or equal to, 220° C.

In one embodiment, the polymerization takes place in the presence of at least one inventive transition metal complex, and optionally one or more other catalyst systems, in one or more polymerization reactors, connected in parallel, series or combinations thereof.

In one embodiment, the ethylene-based polymer has a melt viscosity, at 177° C., less than, or equal to, 50,000 cP, further less than, or equal to, 40,000 cP, further less than, or equal to, 30,000 cP, further less than, or equal to, 20,000 cP.

In one embodiment, the ethylene-based polymer is an ethylene/α-olefin interpolymer, and further an ethylene/α-olefin copolymer. Preferred α-olefins include, but are not limited to, C3-C20 α-olefins, and further C3-C10 α-olefins. More preferred α-olefins include propylene, 1-butene, 1-pentene, 1-hexene, 1-heptene and 1-octene, and more further include propylene, 1-butene, 1-hexene and 1-octene, further 1-butene, 1-hexene and 1-octene, further 1-butene and 1-octene.

The invention also provides an ethylene-based polymer formed from the process of one or more embodiments described herein.

In one embodiment, the polymer has a melt viscosity, at 177° C., less than, or equal to, 50,000 cP, further less than, or equal to, 40,000 cP, further less than, or equal to, 30,000 cP, further less than, or equal to, 20,000 cP.

In one embodiment, the ethylene-based polymer is an ethylene/α-olefin interpolymer, and further an ethylene/α-olefin copolymer. Preferred α-olefins include, but are not limited to, C3-C20 α-olefins, and further C3-C10 α-olefins. More preferred α-olefins include propylene, 1-butene, 1-pentene, 1-hexene, 1-heptene and 1-octene, and more further include propylene, 1-butene, 1-hexene and 1-octene, further 1-butene, 1-hexene and 1-octene, further 1-butene and 1-octene.

In one embodiment, the ethylene-based polymer has a number average molecular weight (Mn) from 2,000 to 50,000 g/mole, further from 3,000 to 40,000, further from 4,000 to 30,000 g/mole.

In one embodiment, the ethylene-based polymer has a number average molecular weight (Mn) from 2,000 to 25,000 g/mole, further from 2,000 to 20,000, further from 2,000 to 15,000 g/mole, further from 2,000 to 10,000 g/mole.

In one embodiment, the ethylene-based polymer has a molecular weight distribution (MWD) from 1.7 to 3.0, further from 1.8 to 2.8, further from 1.9 to 2.7.

The invention also provides a composition comprising an inventive ethylene-based polymer. In a further embodiment, the composition further comprises one or more additives.

The invention also provides an article comprising at least one component formed from an inventive composition.

An inventive ethylene-based polymer may comprise a combination of two or more embodiments described herein.

An inventive composition may comprise a combination of two or more embodiments described herein.

An inventive article may comprise a combination of two or more embodiments described herein.

An inventive process may comprise a combination of two or more embodiments described herein.

The molecular transition metal complex of Formula 1 may comprise a combination of two or more embodiments described herein.

The present invention employs one or more metal-ligand complexes of Formula (I), which is described herein using conventional chemical group terminology. When used to describe certain carbon atom-containing chemical groups (e.g., ($C_1$-$C_{40}$)alkyl), the parenthetical expression ($C_1$-$C_{40}$) can be represented by the form "($C_v$-$C_w$)," which means that the unsubstituted version of the chemical group comprises from a number x carbon atoms to a number y carbon atoms, wherein each v and w independently is an integer as described for the chemical group.

The term "substituted," as used herein, with respect to a chemical compound, refers to a substituent that comprises at least one heteroatom (for example, O, S, N, P, etc.). Substituents include, but are not limited to, the $R^S$ substituents as follows: a halogen atom, a polyfluoro substituent, a perfluoro substituent, $F_3C-$, $FCH_2O-$, $F_2HCO-$, $F_3CO-$, $(R^C)_3Si-$, $(R^C)_3Ge-$, $(R^C)O-$, $(R^C)S-$, $(R^C)S(O)-$, $(R^C)S(O)_2-$, $(R^C)_2P-$, $(R^C)_2N-$, $(R^C)_2C=N-$, $NC-$, $(R^C)C(O)O-$, $(R^C)OC(O)-$, $(R^C)C(O)N(R^C)-$, and $(R^C)_2NC(O)-$; wherein each $R^C$ is independently a substituted or unsubstituted ($C_1$-$C_{30}$)hydrocarbyl, or a substituted or unsubstituted ($C_1$-$C_{30}$) heterohydrocarbyl.

The term "unsubstituted," as used herein, with respect to a chemical compound, refers to the lack of a substituent that comprises at least one heteroatom (for example, O, S, N, P, etc.).

The term "hydrocarbyl," as used herein, refers to a monovalent (monoradical or radical) chemical group containing only hydrogen and carbon atoms.

The term "substituted hydrocarbyl," as used herein, refers to a hydrocarbyl, in which at least one hydrogen atom is substituted with a substituent that comprises at least one heteroatom.

The term "heterohydrocarbyl," as used herein, refers to a hydrocarbyl, in which at least one carbon atom, or CH group, or CH2 group, is substituted with a heteroatom or a chemical group containing at least one heteroatom. Heteroatoms include, but are not limited to, O, N, P and S.

The term "substituted heterohydrocarbyl," as used herein, refers to a heterohydrocarbyl in which at least one hydrogen atom is substituted with a substituent that comprises at least one heteroatom.

The term "hydrocarbylene," as used herein, refers to a divalent (diradical) chemical group containing only hydrogen and carbon atoms.

The term "substituted hydrocarbylene," as used herein, refers to a hydrocarbylene, in which at least one hydrogen atom is substituted with a substituent that comprises at least one heteroatom.

The term "heterohydrocarbylene," as used herein, refers to a hydrocarbylene, in which at least one carbon atom, or CH group, or CH2 group, is substituted with a heteroatom or a chemical group containing at least one heteroatom. Heteroatoms include, but are not limited to, O, N, P and S.

The term "substituted heterohydrocarbylene," as used herein, refers to a heterohydrocarbylene, in which at least one hydrogen atom is substituted with a substituent that comprises at least one heteroatom.

As used herein, the term "$(C_1-C_{40})$hydrocarbyl" refers to hydrocarbon radical of from 1 to 40 carbon atoms. The hydrocarbon radical independently may be aromatic (6 carbon atoms or more) or non-aromatic, saturated or unsaturated, straight chain or branched chain, cyclic (including mono- and poly-cyclic, fused and non-fused polycyclic, including bicyclic; 3 carbon atoms or more) or acyclic, or a combination of two or more thereof; and each hydrocarbon radical independently is the same as, or different from, another hydrocarbon radical, respectively. The hydrocarbon radical may be optionally substituted with one or more $R^S$ substituents, as defined above (e.g., a substituted hydrocarbyl).

Preferably, a $(C_1-C_{40})$hydrocarbyl is independently a $(C_1-C_{40})$alkyl, or a $(C_3-C_{40})$cycloalkyl. More preferably, each of the aforementioned $(C_1-C_{40})$hydrocarbyl groups independently has a maximum of 20 carbon atoms (i.e., $(C_1-C_{20})$hydrocarbyl), and still more preferably a maximum of 12 carbon atoms. Further, the $(C_1-C_{40})$hydrocarbyl is optionally substituted with one or more $R^S$ substituents, as defined above (e.g., a substituted hydrocarbyl).

As used herein, the term "$(C_1-C_{40})$hydrocarbylene" refers to a hydrocarbon diradical of from 1 to 40 carbon atoms. The hydrocarbon diradical independently may be aromatic (6 carbon atoms or more) or non-aromatic, saturated or unsaturated, straight chain or branched chain, cyclic (including mono- and poly-cyclic, fused and non-fused polycyclic, including bicyclic; 3 carbon atoms or more) or acyclic, or a combination of two or more thereof; and each hydrocarbon diradical independently is the same as, or different from, another hydrocarbon diradical, respectively. Further the hydrocarbon diradical may be optionally substituted with one or more $R^S$ substituents, as defined above (e.g., a substituted hydrocarbylene).

Preferably, a $(C_1-C_{40})$hydrocarbylene, independently, is a $(C_3-C_{20})$cycloalkyl-(C1-$C_{20}$)alkylene, $(C_6-C_{40})$aryl, or $(C_6-C_{20})$aryl-(C1-$C_{20}$)alkylene. More preferably, each of the aforementioned $(C_1-C_{40})$hydrocarbylene groups independently has a maximum of 20 carbon atoms (i.e., $(C_1-C_{20})$hydrocarbyl), and still more preferably a maximum of 12 carbon atoms. The $(C_1-C_{40})$hydrocarbylene may be optionally substituted with one or more $R^S$ substituents, as defined above (e.g., a substituted hydrocarbylene).

The term "$(C_1-C_{40})$heterohydrocarbyl" refers to a heterohydrocarbon radical of from 1 to 40 carbon atoms. The heterohydrocarbyl, independently, has one or more heteroatoms, for example, O; S; S(O); S(O)$_2$; Si($R^C$)$_2$; P($R^P$); and N($R^N$), wherein independently each $R^C$ is unsubstituted $(C_1-C_{18})$hydrocarbyl, each $R^P$ is unsubstituted $(C_1-C_{18})$hydrocarbyl; and each $R^N$ is unsubstituted $(C_1-C_{18})$hydrocarbyl or absent (e.g., absent when N comprises —N═ or tri-carbon substituted N). The heterohydrocarbon radical is on a carbon atom or heteroatom thereof, although preferably is on a carbon atom when bonded to a heteroatom in Formula (I) or to a heteroatom of another heterohydrocarbyl. The $(C_1-C_{40})$heterohydrocarbyl independently may be saturated or unsaturated, straight chain or branched chain, cyclic (including mono- and poly-cyclic, fused and non-fused polycyclic) or acyclic, or a combination of two or more thereof; and each is respectively the same as or different from another. Substituted heterohydrocarbyls are discussed above.

The term "$(C_1-C_{40})$heterohydrocarbylene refers to a heterohydrocarbon diradical of from 1 to 40 carbon atoms. The heterohydrocarbylene, independently, has one or more heteroatoms, for example, O; S; S(O); S(O)$_2$; Si($R^C$)$_2$; Ge($R^C$)$_2$; P($R^P$); and N($R^N$), wherein independently each $R^C$ is unsubstituted $(C_1-C_{18})$hydrocarbyl, each $R^P$ is unsubstituted $(C_1-C_{18})$hydrocarbyl; and each $R^N$ is unsubstituted $(C_1-C_{18})$hydrocarbyl or absent (e.g., absent when N comprises —N═ or tri-carbon substituted N). The heterohydrocarbon radical and each of the heterohydrocarbon diradicals independently is on a carbon atom or heteroatom thereof, although preferably is on a carbon atom when bonded to a heteroatom in Formula (I) or to a heteroatom of another heterohydrocarbyl or heterohydrocarbylene. The $(C_1-C_{40})$-heterohydrocarbylene independently is unsubstituted or substituted (for example, by one or more $R^S$), aromatic or non-aromatic, saturated or unsaturated, straight chain or branched chain, cyclic (including mono- and poly-cyclic, fused and non-fused polycyclic) or acyclic, or a combination of two or more thereof; and each is respectively the same as or different from another. Substituted heterohydrocarbylenes are discussed above.

Preferably, the $(C_1-C_{40})$heterohydrocarbyl independently is $(C_1-C_{40})$heteroalkyl, $(C_1-C_{40})$hydrocarbyl-O—, $(C_1-C_{40})$hydrocarbyl-S—, $(C_1-C_{40})$hydrocarbyl-S(O)—, $(C_1-C_{40})$hydrocarbyl-S(O)$_2$—, $(C_1-C_{40})$hydrocarbyl-Si($R^C$)$_2$—, $(C_1-C_{40})$hydrocarbyl-Ge($R^C$)$_2$—, $(C_1-C_{40})$hydrocarbyl-N($R^N$)—, $(C_1-C_{40})$hydrocarbyl-P($R^P$)—, $(C_2-C_{40})$heterocycloalkyl.

Preferably, the $(C_1-C_{40})$heterohydrocarbylene independently is $(C_2-C_{19})$hetero-cycloalkyl-$(C_1-C_{20})$alkylene, $(C_3-C_{20})$cycloalkyl-$(C_1-C_{19})$heteroalkylene, $(C_2-C_{19})$heterocycloalkyl-(C1-$C_{20}$)heteroalkylene, $(C_1-C_{40})$heteroarylene, $(C_1-C_{19})$heteroaryl-$(C_1-C_{20})$alkylene, $(C_6-C_{20})$aryl-$(C_1-C_{19})$heteroalkylene, or $(C_1-C_{19})$heteroaryl-$(C_1-C_{20})$heteroalkylene.

The term "halogen atom" refers to a fluorine atom radical (F), chlorine atom radical (Cl), bromine atom radical (Br), or iodine atom radical (I). Preferably each halogen atom independently is a Br, F, or Cl radical, and more preferably a F or Cl radical, and more preferably a F radical.

Preferably, there are no O—O, S—S, or O—S bonds, other than O—S bonds in an S(O) or S(O)$_2$ diradical functional group, in the transition metal complex of Formula 1. More preferably, there are no O—O, N—N, P—P, N—P, S—S, or O—S bonds, other than O—S bonds in an S(O) or S(O)$_2$ diradical functional group, in the transition metal complex of Formula 1.

The term "saturated" means lacking carbon-carbon double bonds, carbon-carbon triple bonds, and (in heteroatom-containing groups) carbon-nitrogen, carbon-phosphorous, carbon-oxygen, and carbon-silicon multiple bonds.

The term "unsaturated" means containing one or more carbon-carbon double bonds, carbon-carbon triple bonds, and (in heteroatom-containing groups) carbon-nitrogen, carbon-phosphorous, carbon-oxygen, and/or carbon-silicon multiple bonds.

The metal M of Formula 1 is preferably selected from zirconium (Zr), hafnium (Hf), and titanium (Ti), and preferably from Zr or Hf, and more preferably Zr. In some embodiments, M is in a formal oxidation state of +2, +3, or +4. In some embodiments, n is 0, 1, 2, or 3. Each X independently is a monodentate ligand that is neutral, monoanionic, or dianionic; or two Xs are taken together to form a bidentate ligand that is neutral, monoanionic, or dianionic. X and n are chosen, in such a way, that the metal-ligand complex of Formula 1 is, overall, neutral. In some embodiments each X, independently, is the monodentate ligand. In one embodiment, when there are two or more X monodentate ligands, each X is the same. In some embodiments the monodentate ligand is the monoanionic ligand. The monoanionic ligand has a net formal oxidation state of −1. Each monoanionic ligand may independently be hydride, ($C_1$-$C_{40}$)hydrocarbyl carbanion, ($C_1$-$C_{40}$)heterohydrocarbyl carbanion, halide, nitrate, carbonate, phosphate, sulfate, HC(O)O−, ($C_1$-$C_{40}$)hydrocarbylC(O)O−, HC(O)N(H)−, ($C_1$-$C_{40}$)hydrocarbylC(O)N(H)−, ($C_1$-$C_{40}$)hydrocarbylC(O)N(($C_1$-$C_{20}$)hydrocarbyl)−, $R^K R^L B^-$, $R^K R^L N^-$, $R^K O^-$, $R^K S^-$, $R^K R^L P^-$, or $R^M R^K R^L Si^-$, wherein each $R^K$, $R^L$, and $R^M$ independently is hydrogen, ($C_1$-$C_{40}$)hydrocarbyl, or ($C_1$-$C_{40}$)heterohydrocarbyl, or $R^K$ and $R^L$ are taken together to form a ($C_2$-$C_{40}$)hydrocarbylene or ($C_1$-$C_{40}$)heterohydrocarbylene and $R^M$ is as defined above.

In some embodiments, at least one monodentate ligand X independently is a neutral ligand. In one embodiment, the neutral ligand is a neutral Lewis base group that is $R^X N$-$R^K R^L$, $R^K OR^L$, $R^K SR^L$, or $R^X PR^K R^L$, wherein each $R^X$ independently is hydrogen, ($C_1$-$C_{40}$)hydro-carbyl, [($C_1$-$C_{10}$)hydrocarbyl]$_3$Si, [($C_1$-$C_{10}$)hydrocarbyl]$_3$Si($C_1$-$C_{10}$)hydrocarbyl, or ($C_1$-$C_{40}$)heterohydrocarbyl and each $R^K$ and $R^L$ independently is as defined above.

In some embodiments, each X is a monodentate ligand that independently is a halogen atom, unsubstituted ($C_1$-$C_{20}$)hydrocarbyl, unsubstituted ($C_1$-$C_{20}$)hydrocarbylC(O)O—, or $R^K R^L N$— wherein each of $R^K$ and $R^L$, independently, is an unsubstituted ($C_1$-$C_{20}$)hydrocarbyl. In some embodiments each monodentate ligand X is a chlorine atom, ($C_1$-$C_{10}$)hydrocarbyl (e.g., ($C_1$-$C_6$)alkyl or benzyl), unsubstituted ($C_1$-$C_{10}$)hydrocarbylC(O)O—, or $R^K R^L N$— wherein each of $R^K$ and $R^L$ independently is an unsubstituted ($C_1$-$C_{10}$)hydrocarbyl.

In some embodiments, there are at least two X, and the two X are taken together to form the bidentate ligand. In some embodiments the bidentate ligand is a neutral bidentate ligand. In one embodiment, the neutral bidentate ligand is a diene of formula ($R^D$)$_2$C=C($R^D$)—C($R^D$)=C($R^D$)$_2$, wherein each $R^D$, independently, is H, unsubstituted ($C_1$-$C_6$)alkyl, phenyl, or naphthyl. In some embodiments, the bidentate ligand is a monoanionic-mono(Lewis base) ligand. The monoanionic-mono(Lewis base) ligand may be a 1,3-dionate of formula (D): $R^E$—C(O−)=CH—C(=O)—$R^E$ (D), wherein each $R^E$, independently, is H, unsubstituted ($C_1$-$C_6$)alkyl, phenyl, or naphthyl. In some embodiments, the bidentate ligand is a dianionic ligand. The dianionic ligand has a net formal oxidation state of −2. In one embodiment, each dianionic ligand independently is carbonate, oxalate (i.e., −O$_2$CC(O)O−), ($C_2$-$C_{40}$)hydrocarbylene dicarbanion, ($C_1$-$C_{40}$)heterohydrocarbylene dicarbanion, phosphate, or sulfate.

As previously mentioned, number and charge (neutral, monoanionic, dianionic) of X are selected, depending on the formal oxidation state of M, such that the transition metal complex of Formula 1 is overall, neutral.

In some embodiments, each X is the same, wherein each X is methyl; ethyl; 1-propyl; 2-propyl; 1-butyl; 2,2,-dimethylpropyl; trimethylsilylmethyl; phenyl; benzyl; or chloro. In some embodiments, n is 2, and each X is the same, and further each X is methyl; ethyl; 1-propyl; 2-propyl; 1-butyl; 2,2,-dimethylpropyl; trimethylsilylmethyl; phenyl; benzyl; or chloro.

In some embodiments, at least two X are different. In some embodiments, n is 2, and each X is a different one of methyl; ethyl; 1-propyl; 2-propyl; 1-butyl; 2,2,-dimethylpropyl; trimethylsilylmethyl; phenyl; benzyl; or chloro.

The integer n indicates the number of X groups. In one embodiment, n is 2 or 3, and at least two X, independently, are monoanionic monodentate ligands, and a third X, if present, is a neutral monodentate ligand. In some embodiments n is 2, and two X are taken together to form a bidentate ligand. In some embodiments, the bidentate ligand is 2,2-dimethyl-2-silapropane-1,3-diyl or 1,3-butadiene.

In one embodiment, each Z independently is O, S, —N[($C_1$-$C_{40}$)hydrocarbyl]-, or —P[($C_1$-$C_{40}$)hydrocarbyl]-. In some embodiments, each Z is different. In some embodiments, one Z is O, and one Z is —N[($C_1$-$C_{40}$)hydrocarbyl]- (e.g., —N(CH$_3$)—). In some embodiments, one Z is O, and one Z is S. In some embodiments, one Z is S, and one Z is —N[($C_1$-$C_{40}$)hydro-carbyl]- (e.g., —N(CH$_3$)—). In some embodiments, each Z is the same. In some embodiments, each Z is O. In some embodiments, each Z is S. In some embodiments, each Z is —N[($C_1$-$C_{40}$)-hydrocarbyl]- (e.g., —N(CH$_3$)—). In some embodiments, at least one, and in some embodiments each Z, is —P[($C_1$-$C_{40}$)hydrocarbyl]- (e.g., —P(CH$_3$)—).

Polymerization

In order to prepare the homopolymers, interpolymers, or copolymers of the invention, ethylene and/or the selected alpha-olefin monomer(s) is/are fed into a suitable reactor, for batch, semi-continuous, or continuous production, wherein such monomer(s) will come into contact with the catalyst. In the case of preparation of a copolymer, it is noted that the ethylene/alpha-olefin reactivity ratio is distinct for any given catalyst, and provides a methodology to determine the amount of alpha-olefin that will be required to attain a targeted copolymer composition. Reactivity ratios may be determined using well-known theoretical techniques, or empirically derived from actual polymerization data. Suitable theoretical techniques are disclosed, for example, in B. G. Kyle, *Chemical and Process Thermodynamics*, 3$^{rd}$ ed., Prentice-Hall (Englewood Cliffs, N.J. 1999) and in G. Soave, "Redlich-Kwong-Soave (RKS) Equation of State," *Chemical Engineering Science*, 1972, vol. 27, pp 1197-1203. Commercially available software programs may be used to assist in deriving reactivity ratios from experimentally derived data. One example of such software is Aspen Plus from Aspen Technology, Inc., Ten Canal Park, Cambridge, Mass. 02141-2201, USA. In one embodiment, the target amount of alpha-olefin in a copolymer range from 1 to 30 mole percent (mol %); more preferably from 1 to 25 mol %; and still more preferably from 1 to 20 mol %, based on the total moles of polymerized monomers.

The transition metal complex of Formula 1 is rendered catalytically active by contacting it to, or combining it with, the activating co-catalyst, or by using an activating technique, such as those that are known in the art for use with metal-based olefin polymerization reactions. Many activating co-catalysts and activating techniques have been previously taught, with respect to different metal-ligand complexes, in the following patent references: U.S. Pat. No. 5,064,802; U.S. Pat. No. 5,153,157; U.S. Pat. No. 5,296,433; U.S. Pat. No. 5,321,106; U.S. Pat. No. 5,350,723; U.S. Pat. No. 5,425,872; U.S. Pat. No. 5,625,087; U.S. Pat. No. 5,721,185; U.S. Pat. No. 5,783,512; U.S. Pat. No. 5,883,204; U.S. Pat. No. 5,919,983; U.S. Pat. No. 6,696,379; and U.S. Pat. No. 7,163,907. Examples of suitable hydrocarbyloxides are disclosed in U.S. Pat. No. 5,296,433. Examples of suitable Bronsted acid salts for addition polymerization catalysts are disclosed in U.S. Pat. No. 5,064,802; U.S. Pat. No. 5,919,983; U.S. Pat. No. 5,783,512. Examples of suitable salts of a cationic oxidizing agent and a non-coordinating, compatible anion as activating co-catalysts for addition polymerization catalysts are disclosed in U.S. Pat. No. 5,321,106. Examples of suitable carbenium salts as activating co-catalysts for addition polymerization catalysts are disclosed in U.S. Pat. No. 5,350,723. Examples of suitable silylium salts as activating co-catalysts for addition polymerization catalysts are disclosed in U.S. Pat. No. 5,625,087. Examples of suitable complexes of alcohols, mercaptans, silanols, and oximes with tris(pentafluorophenyl)borane are disclosed in U.S. Pat. No. 5,296,433. Some of these catalysts are also described in a portion of U.S. Pat. No. 6,515,155, beginning at column 50, at line 39, and going through column 56, at line 55, only the portion of which is incorporated by reference herein.

In some embodiments, the transition metal complex of Formula 1, may be activated to form an active catalyst composition, by combination with one or more cocatalysts, such as a cation-forming cocatalyst, a strong Lewis acid, or a combination thereof. Suitable cocatalysts include polymeric or oligomeric aluminoxanes, especially methyl aluminoxane, as well as inert, compatible, noncoordinating, ion-forming compounds. Exemplary suitable cocatalysts include, but are not limited to modified methyl aluminoxane (MMAO), triethyl aluminum (TEA), tris-pentafluorophenyl borane, bis-hydrogenatedtallowalkylmethylammonium tetrakis-pentafluoro-phenylborate, and any combination thereof. In one embodiment, the cocatalyst is selected from tris-pentafluorophenyl borane, modified methaluminoxane, bis-hydrogenatedtallowalkylmethylammonium tetrakis-pentafluorophenylborate, and combinations thereof.

In some embodiments, one or more of the foregoing activating co-catalysts are used in combination with each other. An especially preferred combination is a mixture of a tri(($C_1$-$C_4$)hydrocarbyl)aluminum, tri(($C_1$-$C_4$)hydrocarbyl) borane, or an ammonium borate with an oligomeric or polymeric alumoxane compound.

The ratio of total number of moles of one or more transition metal complexes of Formula 1 to total number of moles of one or more of the activating co-catalysts is from 1:10,000 to 100:1. In some embodiments, the ratio is at least 1:5000, in some other embodiments, at least 1:1000 or 1:100; and 10:1 or less, and in some other embodiments, 1:1 or less. When an alumoxane, alone, is used as the activating co-catalyst, preferably the number of moles of the alumoxane employed is at least 10 times, further at least 40 times, further at least 100 times the number of moles of the transition metal complex of Formula 1. When tris(pentafluorophenyl)-borane, alone, is used as the activating co-catalyst, in some other embodiments, the number of moles of the tris(pentafluoro-phenyl)borane employed, to the total number of moles of one or more transition metal complexes of Formula 1, is from 0.5:1 to 10:1, in some other embodiments, from 1:1 to 6:1, in some other embodiments, from 1:1 to 5:1. The remaining activating cocatalysts are generally employed in approximately mole quantities equal to the total mole quantities of one or more transition metal complexes of Formula 1.

A variety of homopolymerization or copolymerization conditions, and combinations thereof, may be employed, according to the starting materials, nature of the reaction (batch, semi-continuous, or continuous), apparatus set-up, desired products, and so forth. However, in general, suitable polymers, interpolymers, or copolymers of the invention, may be produced using one or more of the specified transition metal complexes of Formula 1, at a temperatures preferably from 150° C. to 250° C., further from 160° C. to 240° C., further from 170° C. to 230° C. A reaction time may range from 10 minutes to 300 minutes. Other parameters, such as pressure, may be controlled, and varied, according to the desires and needs of the practitioner. It is usually preferred to carry out the process as a continuous process, further using at least one continuous stirred-tank reactor (CSTR) or other suitable vessel(s); and preferably a continuous solution process, further using at least one continuous stirred-tank reactor (CSTR) or other suitable vessel(s).

Ethylene-Based Polymers

The ethylene-based polymer may be an ethylene homopolymer, an ethylene-based interpolymer, or an ethylene-based copolymer.

In one embodiment, the ethylene-based polymer is an ethylene/α-olefin interpolymer, and further an ethylene/α-olefin copolymer. Preferred α-olefins include, but are not limited to, C3-C20 α-olefins, further C3-C12 α-olefins, and further C3-C10 α-olefins. More preferred α-olefins include propylene, 1-butene, 1-pentene, 1-hexene, 1-heptene and 1-octene, and more further include propylene, 1-butene, 1-hexene and 1-octene, further 1-butene, 1-hexene and 1-octene, further 1-butene and 1-octene.

In non-limiting example only, the α-olefin may be selected from linear alpha-olefins having from 3 to 12 carbons, such as propylene, 1-butene, 1-pentene, 1-hexene, 1-heptene, 1-octene, 1-nonene, 1-decene, undecene, 1-dodecene, and combinations thereof. Smaller linear alpha-olefins having from 3 to 8 carbons are preferred, because they allow for a higher branch density of the final product oligomers. Branched alpha-olefins may also be employed in the process feed, and may include in non-limiting embodiments singly and multiply branched alpha-olefin monomers having from 5 to 16 carbons, wherein the first substituted carbon is at the "3" or greater position with respect to the vinyl, and combinations thereof. It is generally preferred that the first substitution be at the "4" or greater position.

In one embodiment, the ethylene-based polymer has a melt viscosity less than, or equal to, 50,000 cP, further less than, or equal to, 40,000 cP, further less than, or equal to, 30,000 cP, further less than, or equal to, 20,000 cP, at 350° F. (177° C.). In a further embodiment, the ethylene-based polymer is an ethylene/α-olefin interpolymer, and further an ethylene/α-olefin copolymer. Suitable α-olefins are described above.

In one embodiment, the ethylene-based polymer has a melt viscosity greater than, or equal to, 2,000 cP, further greater than, or equal to, 4,000 cP, more further greater than, or equal to, 5,000 cP, at 350° F. (177° C.). In a further embodiment, the ethylene-based polymer is an ethylene/α-olefin interpolymer, and further an ethylene/α-olefin copolymer. Suitable α-olefins are described above.

In one embodiment, the ethylene-based polymer has a melt viscosity from 2,000 cP to 25,000 cP, further from 4,000 cP to 20,000 cP, and further from 5,000 cP to 18,000 cP, at 350° F. (177° C.). In a further embodiment, the ethylene-based polymer is an ethylene/α-olefin interpolymer, and further an ethylene/α-olefin copolymer. Suitable α-olefins are described above.

In one embodiment, the ethylene-based polymer has a molecular weight distribution (Mw/Mn) less than, or equal to, 5.0, and further less than, or equal to, 4.0, and more further less than, or equal to, 3.5. Further the ethylene/α-olefin interpolymers have a molecular weight distribution from 1.5 to 4.0, and further from 2.0 to 3.8, and more further from 2.2 to 3.5. In a further embodiment, the ethylene-based polymer is an ethylene/α-olefin interpolymer, and further an ethylene/α-olefin copolymer. Suitable α-olefins are described above.

In one embodiment, the ethylene-based polymer has a melt index (I2 or MI), or a calculated melt index (I2), greater than, or equal to, 500 g/10 min, further greater than, or equal to, 800 g/10 min, and more further greater than, or equal to, 1000 g/10 min. In a further embodiment, the ethylene-based polymer is an ethylene/α-olefin interpolymer, and further an ethylene/α-olefin copolymer. Suitable α-olefins are described above.

In one embodiment, the ethylene-based polymer has a percent crystallinity of less than, or equal to, 40 percent, further less than, or equal to, 30 percent, and more further less than, or equal to, 20 percent, as determined by DSC. In a further embodiment, the ethylene-based polymer is an ethylene/α-olefin interpolymer, and further an ethylene/α-olefin copolymer. Suitable α-olefins are described above.

In one embodiment, the ethylene-based polymer has a percent crystallinity of greater than, or equal to, 2 percent, further greater than, or equal to, 5 percent, and more further greater than, or equal to, 10 percent, as determined by DSC. In a further embodiment, the ethylene-based polymer is an ethylene/α-olefin interpolymer, and further an ethylene/α-olefin copolymer. Suitable α-olefins are described above.

In one embodiment, the ethylene-based polymer has a percent crystallinity from 2 to 30 percent, further from 5 to 25 percent, and more further from 10 to 20 percent, as determined by DSC. In a further embodiment, the ethylene-based polymer is an ethylene/α-olefin interpolymer, and further an ethylene/α-olefin copolymer. Suitable α-olefins are described above.

In one embodiment, the ethylene-based polymer has a density greater than, or equal to, 0.855 g/cc, further greater than, or equal to, 0.860 g/cc, more further greater than, or equal to, 0.865 g/cc. In a further embodiment, the ethylene-based polymer is an ethylene/α-olefin interpolymer, and further an ethylene/α-olefin copolymer (1 cc=1 cm$^3$). Suitable α-olefins are described above.

In one embodiment, the ethylene-based polymer has a density less than, or equal to, 0.900 g/cc, further less than, or equal to, 0.895 g/cc, more further less than, or equal to, 0.890 g/cc. In a further embodiment, the ethylene-based polymer is an ethylene/α-olefin interpolymer, and further an ethylene/α-olefin copolymer. Suitable α-olefins are described above.

In one embodiment, the ethylene-based polymer has a density from 0.855 g/cc to 0.900 g/cc, further from 0.860 g/cc to 0.895 g/cc, and more further from 0.865 g/cc to 0.890 g/cc. In a further embodiment, the ethylene-based polymer is an ethylene/α-olefin interpolymer, and further an ethylene/α-olefin copolymer. Suitable α-olefins are described above.

In one embodiment, the ethylene-based polymer has a density from 0.862 g/cc to 0.885 g/cc, further from 0.865 g/cc to 0.882 g/cc, and more further from 0.868 g/cc to 0.880 g/cc. In a further embodiment, the ethylene-based polymer is an ethylene/α-olefin interpolymer, and further an ethylene/α-olefin copolymer. Suitable α-olefins are described above.

In one embodiment, the ethylene/α-olefin interpolymer is a homogeneously branched linear interpolymer, and further a copolymer, or a homogeneous branched substantially linear interpolymer, and further a copolymer. Suitable α-olefins are described above.

In one embodiment, the ethylene/α-olefin interpolymer is a homogeneously branched linear interpolymer, and further a copolymer. Suitable α-olefins are described above.

In one embodiment, the ethylene/α-olefin interpolymer is a homogeneous branched substantially linear interpolymer, and further a copolymer. Suitable α-olefins are described above.

The terms "homogeneous" and "homogeneously-branched" are used in reference to an ethylene/α-olefin interpolymer, in which the α-olefin comonomer is randomly distributed within a given polymer molecule, and all of the polymer molecules have the same or substantially the same comonomer-to-ethylene ratio.

The homogeneously branched linear ethylene interpolymers are ethylene polymers, which lack long chain branching, but do have short chain branches, derived from the comonomer polymerized into the interpolymer, and which are homogeneously distributed, both within the same polymer chain, and between different polymer chains. These ethylene interpolymers (for example, homogeneously branched linear ethylene/α-olefin interpolymers) have a linear polymer backbone, no measurable long chain branching, and a narrow molecular weight distribution. This class of polymers is disclosed, for example, by Elston in U.S. Pat. No. 3,645,992, and subsequent processes to produce such polymers, using bis-metallocene catalysts, have been developed, as shown, for example, in EP 0 129 368; EP 0 260 999; U.S. Pat. No. 4,701,432; U.S. Pat. No. 4,937,301; U.S. Pat. No. 4,935,397; U.S. Pat. No. 5,055,438; and WO 90/07526; each incorporated herein by reference. As discussed, the homogeneously branched linear ethylene interpolymers lack long chain branching, just as is the case for the linear low density polyethylene polymers or linear high density polyethylene polymers. Commercial examples of homogeneously branched linear ethylene/α-olefin interpolymers include TAFMER polymers from the Mitsui Chemical Company, and EXACT and EXCEED polymers from ExxonMobil Chemical Company.

The homogeneously branched substantially linear ethylene/α-olefin interpolymers are described in U.S. Pat. Nos. 5,272,236; 5,278,272; 6,054,544; 6,335,410 and 6,723,810; each incorporated herein by reference. The substantially linear ethylene/α-olefin interpolymers have long chain branching. The long chain branches have the same comonomer distribution as the polymer backbone, and can have about the same length as the length of the polymer backbone. "Substantially linear," typically, is in reference to a polymer that is substituted, on average, with "0.01 long chain branches per 1000 total carbons" to "3 long chain branches per 1000 total carbons." The length of a long chain branch is longer than the carbon length of a short chain branch, formed from the incorporation of one comonomer into the polymer backbone.

Some polymers may be substituted with 0.01 long chain branches per 1000 total carbons to 3 long chain branch per 1000 total carbons, further from 0.01 long chain branches per 1000 total carbons to 2 long chain branch per 1000 total carbons, and further from 0.01 long chain branches per 1000 total carbons to 1 long chain branch per 1000 total carbons.

The substantially linear ethylene/α-olefin interpolymers form a unique class of homogeneously branched ethylene polymers. They differ substantially from the well-known class of conventional, homogeneously branched linear ethylene/α-olefin interpolymers, as discussed above, and, moreover, they are not in the same class as conventional heterogeneous "Ziegler-Natta catalyst polymerized" linear ethylene polymers (for example, ultra low density polyethylene (ULDPE), linear low density polyethylene (LLDPE) or high density polyethylene (HDPE), made, for example, using the technique disclosed by Anderson et al., in U.S. Pat. No. 4,076,698); nor are they in the same class as high pressure, free-radical initiated, highly branched polyethylenes, such as, for example, low density polyethylene (LDPE), ethylene-acrylic acid (EAA) copolymers and ethylene vinyl acetate (EVA) copolymers.

The homogeneously branched, substantially linear ethylene/α-olefin interpolymers useful in the invention have excellent processability, even though they have a relatively narrow molecular weight distribution. Surprisingly, the melt flow ratio (110/12), according to ASTM D 1238, of the substantially linear ethylene interpolymers can be varied widely, and essentially independently of the molecular weight distribution (Mw/Mn or MWD). This surprising behavior is contrary to conventional homogeneously branched linear ethylene interpolymers, such as those described, for example, by Elston in U.S. Pat. No. 3,645,992, and heterogeneously branched, conventional "Ziegler-Natta polymerized," linear polyethylene interpolymers, such as those described, for example, by Anderson et al., in U.S. Pat. No. 4,076,698. Unlike substantially linear ethylene interpolymers, linear ethylene interpolymers (whether homogeneously or heterogeneously branched) have rheological properties, such that, as the molecular weight distribution increases, the 110/12 value also increases.

Long chain branching can be determined by using 13C Nuclear Magnetic Resonance (NMR) spectroscopy, and can be quantified using the method of Randall (Rev. Macromol. Chem. Phys., C29 (2 &3), 1989, p. 285-297), the disclosure of which is incorporated herein by reference. Two other methods are Gel Permeation Chromatography, coupled with a Low Angle Laser Light Scattering detector (GPCLALLS), and Gel Permeation Chromatography, coupled with a Differential Viscometer detector (GPC-DV). The use of these techniques for long chain branch detection, and the underlying theories, have been well documented in the literature. See, for example, Zimm, B. H. and Stockmayer, W. H., J. Chem. Phys., 17, 1301 (1949), and Rudin, A., Modern Methods of Polymer Characterization, John Wiley & Sons, New York (1991) pp. 103-112.

In contrast to "substantially linear ethylene polymer," "linear ethylene polymer" means that the polymer lacks measurable or demonstrable long chain branches, that is, the polymer is substituted with an average of less than 0.01 long chain branch per 1000 total carbons.

The ethylene-based polymer may comprise a combination of two or more embodiments as described herein.

The ethylene/α-olefin interpolymer may comprise a combination of two or more embodiments as described herein.

The ethylene/α-olefin copolymer may comprise a combination of two or more embodiments as described herein.

Additives and Applications

An inventive composition may further comprise one or more additives. Typically polymers and resins are treated with one or more stabilizers, for example, antioxidants, such as IRGANOX 1010, IRGANOX 1076, and IRGAFOS 168, each supplied by BASF. Polymers are typically treated with one or more stabilizers before an extrusion or other melt processes. Other additives include, but are not limited to, ultraviolet light absorbers, antistatic agents, pigments and dyes, nucleating agents, fillers, slip agents, fire retardants, plasticizers, processing aids, lubricants, stabilizers, smoke inhibitors, viscosity control agents and anti-blocking agents. An inventive composition may also contain one or more thermoplastic polymers.

The inventive compositions may further comprise an oil. Oils are typically employed to reduce the viscosity of the adhesive. When employed, oils will be typically present in an amount less than 50, preferably less than 40, and more preferably less than 35 weight percent, based on the weight of the composition. Exemplary classes of oils include, but are not limited to, white mineral oil (such as KAYDOL oil available from Witco), and SHELLFLEX 371 naphthenic oil (available from Shell Oil Company) and CALSOL 5550 (napthenic oil from Calumet Lubricants).

An inventive composition may comprise from 20 to 60 weight percent, further from 30 to 50 weight percent of a tackifier, based on the weight of the composition. An inventive composition may comprise from 10 to 40 weight percent, further from 10 to 30 weight percent of an oil, based on the weight of the composition.

An inventive composition may comprise from 20 to 60 weight percent, further from 30 to 50 weight percent of a tackifier, based on the weight of the composition. An inventive composition may comprise from 10 to 40 weight percent, further from 10 to 30 weight percent of a wax, based on the weight of the composition.

The inventive compositions may be prepared by standard melt blending procedures. In particular, the ethylene-based polymer, tackifier, oil and/or wax and/or other components may be melt blended until a homogeneous mix is obtained. Any mixing method producing a homogeneous blend, without degrading the adhesive components, is satisfactory, such as a vessel equipped with a stirrer, and an optional heating mechanism. The adhesives can be provided in forms, such as pellets, pillows, chiclets, drages or any other desired configurations.

The inventive compositions may also be used in a variety of applications, including, but not limited to, case and carton sealing, automotive, graphic arts, nonwovens, panel assembly, high performance tapes, contact hot melt adhesives, paperboard coatings, inks, personal care and cosmetic products, sealants, color and additive concentrates, carpet-tape adhesives, woodworking adhesives, and profile wrap adhesives.

Definitions

Unless stated to the contrary, all test methods are current as of the filing date of this disclosure.

The term "composition," as used herein, includes a mixture of materials which comprise the composition, as well as reaction products and decomposition products formed from the materials of the composition.

The term "polymer," as used herein, refers to a polymeric compound prepared by polymerizing monomers, whether of the same or a different type. The generic term polymer thus embraces the term homopolymer (employed to refer to polymers prepared from only one type of monomer, with the understanding that trace amounts of impurities can be incorporated into the polymer structure), and the term interpolymer as defined hereinafter. Trace amounts of impurities, for example, catalyst residues, may be incorporated into and/or within the polymer.

The term "interpolymer," as used herein, refers to polymers prepared by the polymerization of at least two different types of monomers. The generic term interpolymer thus includes copolymers (employed to refer to polymers prepared from two different types of monomers), and polymers prepared from more than two different types of monomers.

The term, "ethylene-based polymer," as used herein, refers to a polymer that comprises, in polymerized form, a majority amount of ethylene monomer (based on the weight of the polymer), and optionally may comprise one or more comonomers.

The term, "ethylene-based interpolymer," as used herein, refers to an interpolymer that comprises, in polymerized form, a majority amount of ethylene monomer (based on the weight of the interpolymer), and at least one comonomer.

The term, "ethylene-based copolymer," as used herein, refers to a copolymer that comprises, in polymerized form, a majority amount of ethylene monomer (based on the weight of the copolymer), and a comonomer, as the only two monomer types.

The term, "ethylene/α-olefin interpolymer," as used herein, refers to an interpolymer that comprises, in polymerized form, a majority amount of ethylene monomer (based on the weight of the interpolymer), and at least one α-olefin.

The term, "ethylene/α-olefin copolymer," as used herein, refers to a copolymer that comprises, in polymerized form, a majority amount of ethylene monomer (based on the weight of the copolymer), and an α-olefin, as the only two monomer types.

The term, "propylene-based polymer," as used herein, refers to a polymer that comprises, in polymerized form, a majority amount of propylene monomer (based on the weight of the polymer), and optionally may comprise one or more comonomers.

The terms "comprising," "including," "having," and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed.

Test Methods

Melt Viscosity

Melt viscosity is measured in accordance with ASTM D 3236 (177° C., 350° F.), using a Brookfield Digital Viscometer (Model DV-III, version 3), and disposable aluminum sample chambers. The spindle is a SC-31 hot-melt spindle, suitable for measuring viscosities in the range from 10 to 100,000 centipoise (cP). The sample is poured into the chamber, which is, in turn, inserted into a Brookfield Thermosel, and locked into place. The sample chamber has a notch on the bottom that fits the bottom of the Brookfield Thermosel, to ensure that the chamber is not allowed to turn when the spindle is inserted and spinning. The sample (approximately 8-10 grams of resin) is heated to the required temperature, until the melted sample is about one inch below the top of the sample chamber. The viscometer apparatus is lowered, and the spindle submerged into the sample chamber. Lowering is continued, until the brackets on the viscometer align on the Thermosel. The viscometer is turned on, and set to operate at a shear rate, which leads to a torque reading in the range from 40 to 60 percent of the total torque capacity, based on the rpm output of the viscometer. Readings are taken every minute, for about 15 minutes, or until the values stabilize, at which point, a final reading is recorded.

Melt Index

Melt index (I2, or MI) of an ethylene-based polymer is measured in accordance with ASTM D-1238, condition 190° C./2.16 kg. For high I2 polymers (I2 greater than, or equal to, 200 g/mole), the melt index is preferably calculated from Brookfield viscosity as described in U.S. Pat. Nos. 6,335,410; 6,054,544; 6,723,810. I2(190° C./2.16 kg)=3.6126[$10^{(log(\eta)-60.6928)/-10.1363}$]−9.31851, where η=melt viscosity, in cP, at 350° F.

Gel Permeation Chromatography (GPC)

The average molecular weights and molecular weight distributions for ethylene-based polymers are determined with a chromatographic system, consisting of either a Polymer Laboratories Model PL-210 or a Polymer Laboratories Model PL-220. The column and carousel compartments are operated at 140° C. for ethylene-based polymers. The columns are three Polymer Laboratories 10-micron, Mixed-B columns. The solvent is 1,2,4-trichloro-benzene. The samples are prepared at a concentration of "0.1 gram of polymer' in "50 milliliters" of solvent. The solvent used to prepare the samples contains "200 ppm of butylated hydroxytoluene (BHT)." Samples are prepared by agitating lightly for two hours at 160° C. The injection volume is "100 microliters," and the flow rate is "1.0 milliliters/minute." Calibration of the GPC column set is performed with "narrow molecular weight distribution" polystyrene standards, purchased from Polymer Laboratories (UK). The polystyrene standard peak molecular weights are converted to polyethylene molecular weights, using the following equation (as described in Williams and Ward, J. Polym. Sci., Polym. Let., 6, 621 (1968)):

$$M_{polyethylene} = A \times (M_{polystyrene})^B,$$

where M is the molecular weight, A has a value of 0.4315 and B is equal to 1.0. Polyethylene equivalent molecular weight calculations were performed using VISCOTEK TriSEC software Version 3.0. The molecular weights for propylene-based polymers can be determined using Mark-Houwink ratios according to ASTM D6474.9714-1, where, for polystyrene a=0.702 and log K=−3.9, and for polypropylene, a=0.725 and log K=−3.721. For propylene-based polymer samples, the column and carousel compartments are operated at 160° C.

Differential Scanning Calorimetry (DSC)

Differential Scanning Calorimetry (DSC) is used to measure crystallinity in ethylene (PE)-based polymer samples and propylene (PP)-based polymer samples. About five to eight milligrams of sample is weighed and placed in a DSC pan. The lid is crimped on the pan to ensure a closed atmosphere. The sample pan is placed in a DSC cell, and then heated, at a rate of approximately 10° C./min, to a temperature of 180° C. for PE (230° C. for PP). The sample is kept at this temperature for three minutes. Then the sample is cooled at a rate of 10° C./min to −60° C. for PE (−40° C. for PP), and kept isothermally at that temperature for three minutes. The sample is next heated at a rate of 10° C./min, until complete melting (second heat). The percent crystallinity is calculated by dividing the heat of fusion ($H_f$), determined from the second heat curve, by a theoretical heat of fusion of 292 J/g for PE (165 J/g, for PP), and multiplying this quantity by 100 (e.g., for PE, % cryst.=($H_f$/292 J/g)× 100; and for PP, % cryst.=($H_f$/165 J/g)×100).

Unless otherwise stated, melting point(s) ($T_m$) of each polymer is determined from the second heat curve obtained from DSC, as described above. The crystallization temperature ($T_c$) is measured from the first cooling curve.

Density

Polymer samples that are measured for density are prepared according to ASTM D-1928. Measurements are made within one hour of sample pressing, using ASTM D-792, Method B.

EXAMPLES

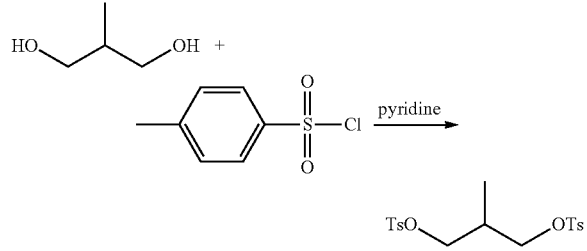

Preparation of 2-methylpropane-1,3-diylbis(4-methylbenzenesulfonate)

To a solution of 4-methylbenzene-1-sulfonylchloride (13.33 g, 69.91 mmol), in anhydrous pyridine (100 mL), at 0° C., was added 2-methylpropane-1,3-diol (3.00 g, 33.29 mmol) in anhydrous pyridine (25 mL), drop-wise, over a period of 2 hours. The reaction mixture was stirred for an additional 4 hours, after which time, it was poured into a mixture of ice (200 mL) and water (50 mL). The aqueous layer was extracted with ethyl acetate (100 mL) three times. The organic phases were combined, and washed with 1M aqueous hydrochloric acid (200 mL), water (200 mL), and brine (200 mL), and dried over anhydrous magnesium sulfate, filtered, and concentrated. Recrystallization was attempted from hexanes. A white precipitate formed in the lower portion of the solvent, and a majority of the hexanes was decanted off, and the sample was placed under high-vacuum. The product solidified, to afford 6.26 g. (62.4%) as white crystals. $^1$H NMR (400 MHz, CDCl$_3$) δ 7.75-7.70 (m, 4H), 7.36-7.30 (m, 4H), 3.93-3.84 (m, 4H), 2.44 (s, 6H), 2.20-2.10 (m, 1H), 0.90 (d, J=7.0 Hz, 3H). $^{13}$C NMR (101 MHz, CDCl$_3$) δ 145.00, 132.50, 129.92, 127.84, 77.32, 77.00, 76.68, 70.30, 33.00, 21.63, 12.94.

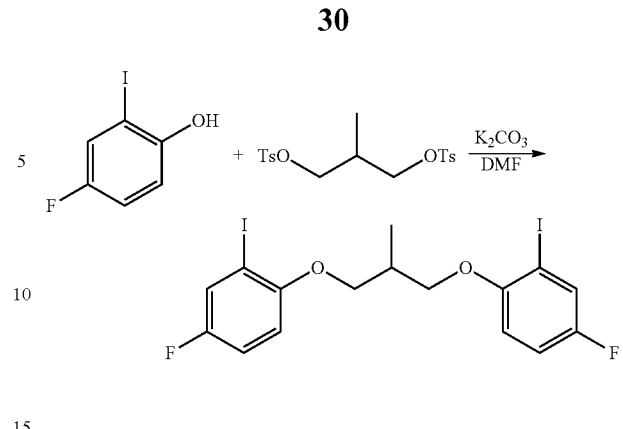

Preparation of 4,4'-((2-methylpropane-1,3-diyl)bis(oxy))bis(1-fluoro-3-iodobenzene)

To a round-bottom flask, was added N,N-dimethylformamide (200 mL), 4-fluoro-2-iodophenol (4.00 g, 16.81 mmol), 2-methylpropane-1,3-diylbis(4-methylbenzenesulfonate) (3.19 g, 8.00 mmol), and potassium carbonate (5.53 g, 40.02 mmol). The reaction mixture was then heated to 120° C., overnight, and then concentrated. The residue was dissolved in a mixture of methylene chloride (100 mL) and water (100 mL). The solution was extracted with methylene chloride (100 mL) two more times. The organic phases were combined, and washed with 2N aqueous sodium hydroxide (200 mL), water (200 mL), and brine (200 mL), dried over anhydrous magnesium sulfate, filtered through a pad of silica, and concentrated. The crude product was recrystallized in hexanes, and collected over a Buchner funnel, to afford 3.64 g. (85.8%) of product as a white powder. $^1$H NMR (400 MHz, CDCl$_3$) δ 7.48 (dd, J=7.6, 3.0 Hz, 2H), 7.01 (ddd, J=9.0, 7.8, 3.0 Hz, 2H), 6.79 (dd, J=9.0, 4.6 Hz, 2H), 4.10 (d, J=5.7 Hz, 4H), 2.61-2.45 (m, 1H), 1.28 (d, J=7.0 Hz, 3H). $^{13}$C NMR (101 MHz, CDCl$_3$) δ 157.96, 155.54, 153.97, 153.94, 126.07, 125.82, 115.72, 115.50, 112.21, 112.13, 85.93, 85.84, 71.14, 33.77, 14.16 (multiplicities due to carbon-fluorine coupling not assigned).

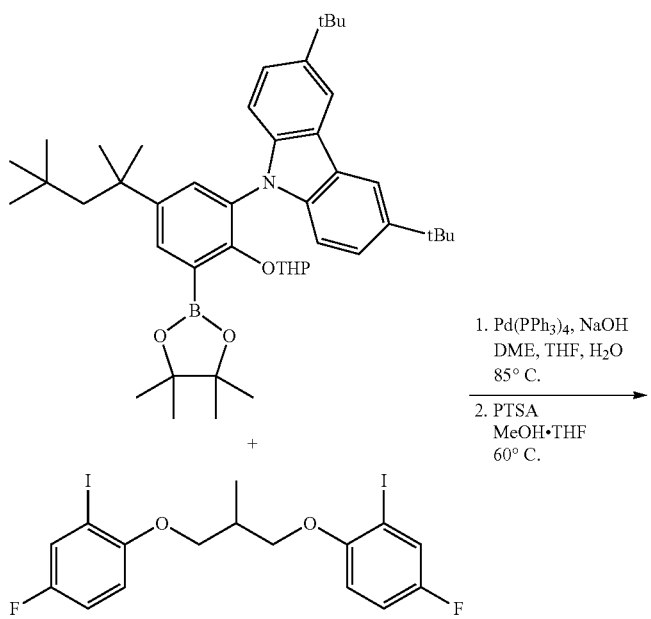

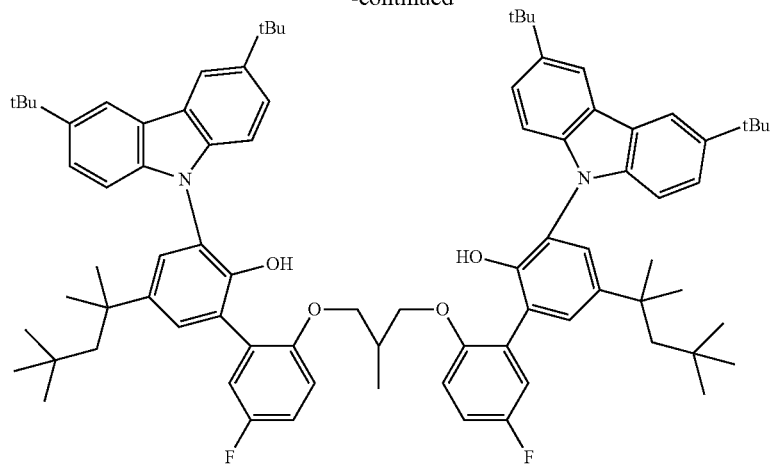

Preparation of 6',6'''-((2-methylpropane-1,3-diylbis(oxy))bis(3-(3,6-di-tert-butyl-9H-carbazol-9-yl)-3'-fluoro-5-(2,4,4-trimethylpentan-2-yl)-[1,1'-biphenyl]-2-ol)

To a round-bottom flask, under $N_2$ atmosphere, was added 3,6-di-tert-butyl-9-(2-(((tetrahydro-2H-pyran-2-yl)oxy)-3-(4,4,5,5-tetramethyl-1,3,2-dioxaborolan-2-yl)-5-(2,4,4-trimethylpentan-2-yl)phenyl)-9H-carbazole (5.35 g, 7.71 mmol), 1,2-dimethoxyethane (200 mL), a solution of sodium hydroxide (0.86 g, 21.62 mmol) in water (60 mL), tetrahydrofuran (60 mL), and 4,4'-((2-methylpropane-1,3-diyl)bis(oxy))bis(1-fluoro-3-iodobenzene) (1.94 g, 3.66 mmol). The system was sparged with $N_2$ for approximately 15 minutes, and tetrakis(triphenylphosphine)-palladium(0) (0.18 g, 0.15 mmol) was added. The mixture was heated to reflux at 85° C. for 48 hours, then allowed to cool and concentrated. The residue was taken up in methylene chloride (200 mL), washed with brine (200 mL), dried over anhydrous magnesium sulfate, filtered through a pad of silica, and concentrated. The crude protected ligand was dissolved in a mixture of tetrahydrofuran (100 mL) and methanol (100 mL), and heated to 60° C. To the solution, was added p-toluenesulfonic acid monohydrate, until the solution became acidic according to pH paper. The mixture was then stirred at 60° C. for 8 hours, then allowed to cool to ambient temperature and concentrated. The residue was dissolved in methylene chloride (200 mL), washed with brine (200 mL), dried over anhydrous magnesium sulfate, filtered through a pad of silica, and concentrated, to give the crude deprotected ligand. The crude ligand was purified via flash chromatography, on an ISCO, through a 330 g column, eluting with 40% methylene chloride in hexanes. The fractions containing product were concentrated, to afford 1.82 g. (40.3%) of the ligand as a white powder. $^1$H NMR (400 MHz, CDCl$_3$) δ 8.25 (dd, J=2.0, 0.6 Hz, 4H), 7.45 (dt, J=8.6, 1.9 Hz, 4H), 7.39 (d, J=2.4 Hz, 2H), 7.24 (d, J=2.4 Hz, 2H), 7.03 (ddd, J=8.6, 6.6, 0.7 Hz, 4H), 6.92 (dd, J=8.7, 3.2 Hz, 2H), 6.40 (ddd, J=8.9, 8.0, 3.2 Hz, 2H), 5.72 (dd, J=9.0, 4.4 Hz, 2H), 5.22 (s, 2H), 3.66 (dd, J=8.9, 4.0 Hz, 2H), 3.56 (dd, J=8.9, 6.3 Hz, 2H), 2.10 (dtd, J=10.8, 6.8, 4.0 Hz, 1H), 1.71 (s, 4H), 1.50 (s, 18H), 1.50 (s, 18H), 1.37 (s, 6H), 1.36 (s, 6H), 0.85 (d, J=7.0 Hz, 3H), 0.80 (s, 18H). $^{13}$C NMR (101 MHz, CDCl$_3$) δ 158.13, 155.75, 151.22, 151.20, 147.97, 142.80, 142.74, 140.05, 140.02, 129.22, 127.82, 127.75, 127.38, 126.17, 126.15, 124.13, 123.67, 123.60, 123.41, 123.36, 118.10, 117.86, 116.33, 115.44, 115.21, 112.48, 112.40, 109.37, 109.35, 69.56, 57.18, 38.21, 34.83, 32.50, 32.17, 31.93, 31.72, 31.63, 13.67 (multiplicities due to carbon-fluorine coupling not assigned). $^{19}$F NMR (376 MHz, CDCl$_3$) δ −122.95−−123.354(m). HRMS (ESI, M+NH$_4^+$): (m/z) calcd for C$_{84}$H$_{106}$F$_2$N$_3$O$_4$ 1258.815, found 1258.813.

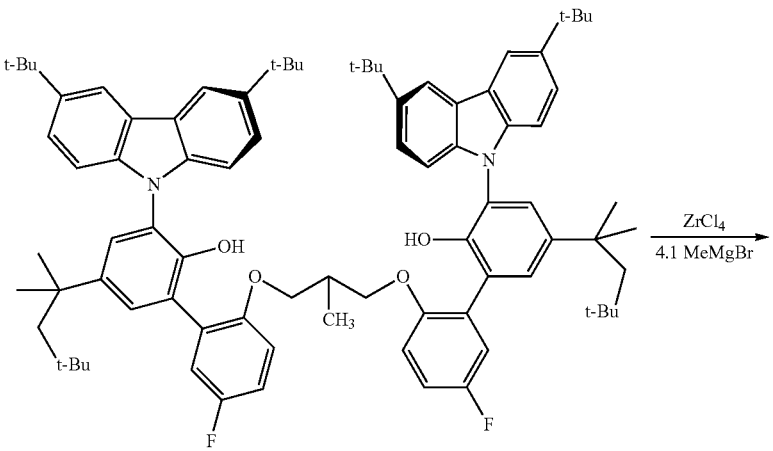

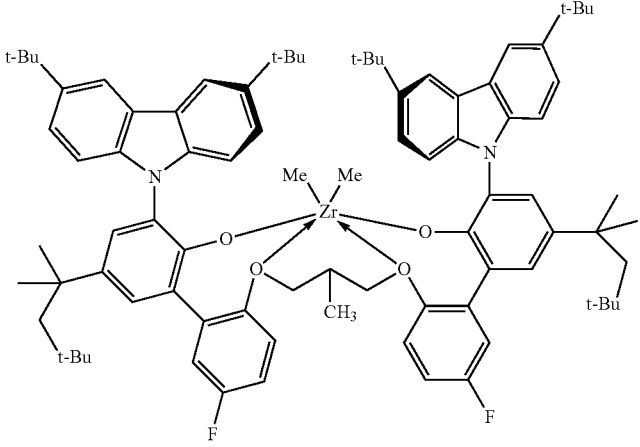

CAT 1

Preparation of CAT 1

To a mixture of the ligand (0.4273 g, 0.34 mmol) and ZrCl$_4$ (0.077 g, 0.34 mmol) suspended in 5 mL of toluene, was added, at ambient temperature, a 3M diethyl ether solution of methylmagnesium bromide (0.48 mL, 1.45 mmol). During the addition, gas evolution was observed. After stirring for 1 hour (black suspension), hexane (10 mL) was added, and the suspension was filtered, giving a colorless solution. Solvent was removed, under reduced pressure, giving 0.4910 g of product. To the product, was added 7 mL of toluene and 8 mL of hexane. The solution was filtered. Solvent was removed under reduced pressure, leaving a white solid. To this solid, was added, 3 mL of hexane, and the suspension was stirred for 1 hour at ambient temperature. The suspension was placed in the freezer for 2 hours. A white solid was collected on a frit, washed with 2 mL of cold hexane, and dried, under reduced pressure, to obtained 250 mg (54%) of final product. $^1$H NMR (400 MHz, C$_6$D6) δ 8.62-8.56 (m, 2H), 8.39 (ddd, J=2.0, 1.4, 0.7 Hz, 2H), 7.68-7.66 (m, 4H), 7.65-7.60 (m, 4H), 7.44 (ddd, J=8.9, 7.1, 1.9 Hz, 2H), 7.23 (dd, J=13.6, 2.5 Hz, 2H), 6.96 (ddd, J=8.9, 4.9, 3.1 Hz, 2H), 6.57 (ddt, J=8.9, 7.4, 3.1 Hz, 2H), 5.10 (dd, J=8.9, 4.9 Hz, 1H), 5.03 (dd, J=8.9, 4.9 Hz, 1H), 3.87-3.78 (m, 1H), 3.69 (ddd, J=9.6, 4.8, 0.7 Hz, 1H), 3.01 (dd, J=11.3, 3.4 Hz, 1H), 2.96 (dd, J=9.5, 8.1 Hz, 1H), 1.69-1.54 (m, 5H), 1.50 (s, 9H), 1.49 (s, 9H), 1.30 (s, 9H), 1.29 (s, 9H), 1.26 (s, 3H), 1.24 (s, 3H), 1.21 (s, 3H), 1.19 (s, 3H), 0.85 (s, 9H), 0.82 (s, 9H), 0.00 (d, J=7.1 Hz, 3H), −0.74 (d, J=0.4 Hz, 3H), −0.82 (d, J=0.5 Hz, 3H). $^{19}$F NMR (376 MHz, C$_6$D$_6$) δ −114.76−−114.91 (m), −115.10−−115.23 (m).

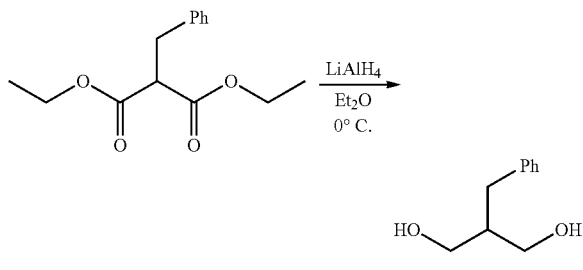

Preparation of 2-benzyl-1,3-propanediol

A three-necked, round-bottomed flask was equipped with a magnetic stir bar, septa, and a nitrogen gas inlet. The flask was charged with a solution of diethyl-2-benzylmalonate (5.00 g, 20.0 mmol) in dried diethyl ether (75 mL). The solution was cooled to 0° C., using an ice water bath, and a 1M solution of lithium aluminum hydride, in THF (80 mL, 80.0 mmol), was slowly added. The resulting solution was stirred at room temperature for 20 hours. While stirring, the reaction was sampled for GC/MS (0.1 mL of sample, 1 drop of water, diluted with ethyl acetate, filtered) for completion, after 3 hours and after 20 hours. Only the starting material was seen in both GC/MS spectra. After 20 hours, the reaction was cooled down to 0° C., using an ice water bath, and water (7.5 mL) was slowly added via an addition funnel. The white salts that formed were filtered off by vacuum filtration, through a pad of celite. The celite was washed with diethyl ether (3×50 mL). The filtrate was dried over magnesium sulfate, filtered by vacuum filtration, and concentrated by rotary evaporation, to afford a crude product as a yellow oil (2.09 g). The celite pad was washed once again with diethyl ether (3×50 mL), to remove any of the crude product that may have been trapped. The filtrate was added to the oil, and solution was concentrated by rotary evaporation, to afford a crude as an yellow oil (2.31 g). The oil was analyzed by $^1$H NMR. The oil was dissolved in a small amount of hexanes, in ethyl acetate, and was purified by column chromatography, using a gradient of 70% ethyl acetate in hexanes, until the product eluted. The fractions were analyzed by TLC.

The pure fractions were combined, and concentrated by rotary evaporation, to afford the product as a white solid. To remove traces of ethyl acetate and hexanes, the solid was dissolved in dichloromethane, and concentrated by rotary evaporation, to afford a white solid (repeated twice). The solid was dried under high vacuum to afford 1.25 g (37.8%). $^1$H NMR (400 MHz, CDCl$_3$, δ 7.28-7.22 (m, 2H), 7.20-7.12 (m, 3H), 3.69 (dt, J=10.7, 4.3 Hz, 2H), 3.57 (dt, J=10.9, 6.9, 4.4 Hz, 2H), 3.51 (t, J=4.8 Hz, 2H), 2.55 (d, J=7.5 Hz, 2H), 1.98 (ddp, J=10.5, 7.2, 3.7 Hz, 1H). $^{13}$C NMR (101 MHz, CDCl$_3$ δ 6 139.95, 129.04, 128.48, 126.16, 77.48, 77.16, 76.84, 64.73, 43.96, 34.31.

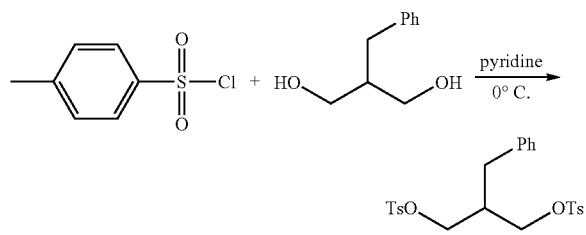

Preparation of 2-benzylpropane-1,3-diyl bis(4-methylbenzenesulfonate)

A three necked round bottom flask was equipped with a magnetic stir bar, septa, and a nitrogen gas inlet. The flask was charged with a solution of 2-benzyl-1,3-propanediol (1.1700 g, 7.039 mmol) in dried pyridine (5 mL). The solution was cooled to 0° C., using an ice water bath, and a solution of para-toluenesulfonyl chloride (2.96 g, 15.5 mmol), in dried pyridine (7 mL), was added slowly. The yellow solution, with precipitate, was stirred at 0° C. for 4 hours, and left overnight in the refrigerator. While stirring at 0° C. for 4 hours, the reaction was sampled by GC/MS (0.1 mL of sample, diluted with ethyl acetate, filtered) for completion, after 1.5 hours and after 4 hours. The reaction was taken out of the refrigerator, and poured into ice cold, 3N aqueous hydrochloric acid (100 mL). The product crashed out of solution as a white solid, while stirring. The mixture was allowed to warm to room temperature. The solid was collected by vacuum filtration, and was washed with water (2×25 mL). The solid was dissolved in dichloromethane, dried over anhydrous magnesium sulfate, filtered by vacuum filtration, and concentrated by rotary evaporation, to afford a murky yellow oil, as a crude product that eventually turned to a solid, while sitting on the bench top for 1-2 hours. The solid was recrystallized from absolute ethanol, collected by vacuum filtration, and dried under high vacuum, to afford 2.07 g (62.3%). $^1$H NMR (500 MHz, CDCl$_3$) δ 7.73 (d, J=8.3 Hz, 4H), 7.34 (d, J=8.0 Hz, 4H), 7.22-7.15 (m, 3H), 6.98-6.91 (m, 2H), 3.98 (dd, J=9.9, 4.7 Hz, 2H), 3.89 (dd, J=9.9, 5.8 Hz, 2H), 2.58 (d, J=7.6 Hz, 2H), 2.47 (s, 6H), 2.30-2.20 (m, 1H). $^{13}$C NMR (101 MHz, CDCl$_3$) δ 144.97, 137.18, 132.23, 129.86, 128.75, 128.47, 127.77, 126.51, 68.12, 39.86, 33.03, 21.54.

inlet. The flask was placed under nitrogen atmosphere, and was charged with N,N-dimethylformamide (34 mL), 4-fluoro-2-iodophenol (2.00 g, 8.41 mmol), 2-benzylpropane-1,3-diyl bis(4-methylbenzenesulfonate) (1.995 g, 4.203 mmol) and potassium carbonate (2.3256 g, 16.827 mmol). This stirred mixture was heated at 100° C., and was sampled by GC/MS analysis (0.1 mL of sample diluted in N,N-dimethylformamide) for completion, after 1 hour and 3 hours. After 3 hours, the reaction was allowed to cool to room temperature, and was stirred at room temperature overnight. The mixture was concentrated to dryness by rotary evaporation, taken up in a 50:50 mixture of dichloromethane:water (8.5 mL:8.5 mL), and extracted with three, 17-mL portions of dichloromethane. The organic phases were combined, and washed with 2N aqueous sodium hydroxide (67 mL), water (67 mL), and then brine (67 mL). The organic phase was dried over magnesium sulfate, filtered through a pad of silica gel by vacuum filtration, and concentrated by rotary evaporation, to afford a crude product as an orange oil (2.2260 g). The oil was dissolved in a small amount of hexanes with some ethyl acetate, and was purified by column chromatography, using a gradient of 5-10% dichloromethane in hexanes for 2 column volumes, then at 10% dichloromethane in hexanes, until the product eluted. The pure fractions were combined, and concentrated by rotary evaporation, to afford the product as a clear oil. To remove traces of hexanes, the oil was dissolved in dichloromethane, and concentrated by rotary evaporation, to a clear oil (repeated twice). The oil was dried under high vacuum, to afford 1.60 g (62.9%). $^1$H NMR (400 MHz, CDCl$_3$, δ 7.48 (dd, J=7.6, 3.0 Hz, 2H), 7.32-7.19 (m, 5H), 6.98 (dddd, J=9.0, 7.9, 3.0, 0.3 Hz, 2H), 6.71 (dd, J=9.0, 4.6 Hz, 2H), 4.15 (dd, J=9.0, 4.7 Hz, 2H), 4.07 (dd, J=9.0, 5.9 Hz, 2H), 3.04 (d, J=7.6 Hz, 2H), 2.61 (ttt, J=7.6, 5.8, 4.6 Hz, 1H). $^{13}$C NMR (101 MHz, CDCl$_3$) δ 157.95, 155.52, 153.77, 153.75, 139.14, 129.18, 128.54, 126.36, 126.03, 125.78, 115.71, 115.50, 115.49, 112.12, 112.04, 85.89, 85.81, 68.66, 40.99, 34.23. $^{19}$F NMR (376 MHz, CDCl$_3$) δ −122.16−−122.24 (m).

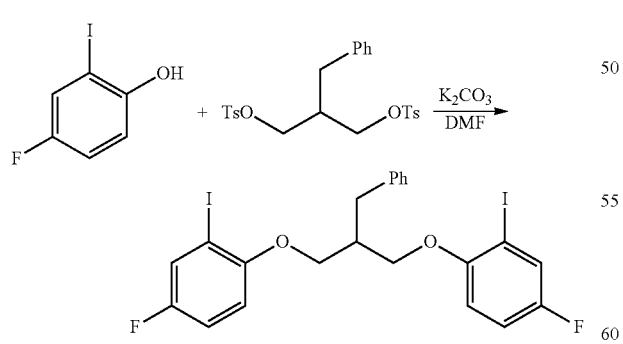

Preparation of 4,4'-((2-benzylpropane-1,3-diyl)bis(oxy))bis(1-fluoro-3-iodobenzene)

A three-necked, round bottom flask was equipped with a magnetic stir bar, septa, a condenser, and a nitrogen gas

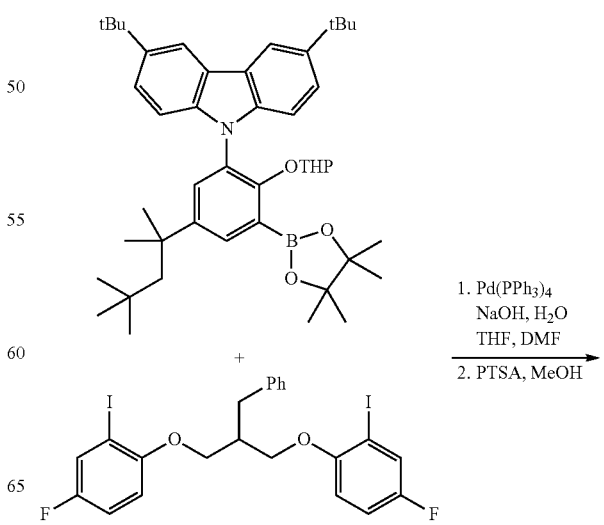

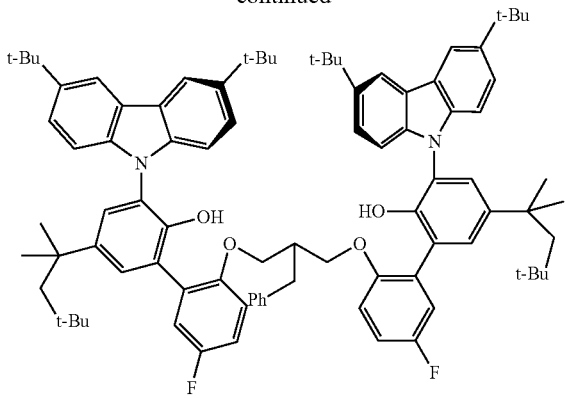

Preparation of 6',6'''-((2-benzylpropane-1,3-diyl)bis(oxy))bis(3-(3,6-di-tert-butyl-9H-carbazol-9-yl)-3'-fluoro-5-(2,4,4-trimethylpentan-2-yl)-[1,1'-biphenyl]-2-ol)

A three-necked, round bottom flask was equipped with a magnetic stir bar, septa, a condenser, and a nitrogen gas inlet. The flask was placed under nitrogen atmosphere, and was charged with 3,6-di-tert-butyl-9-(2-((tetrahydro-2H-pyran-2-yl)oxy)-3-(4,4,5,5-tetramethyl-1,3,2-dioxaborolan-2-yl)-5-(2,4,4-trimethylpentan-2-yl)phenyl)-9H-carbazole (3.696 g, 5.328 mmol), 1,2-dimethoxy-ethane (66 mL), a solution of sodium hydroxide (0.7122 g, 17.81 mmol) in water (19 mL), tetrahydrofuran (22 mL), and 4,4'-((2-benzylpropane-1,3-diyl)bis(oxy))bis(1-fluoro-3-iodobenzene) (1.536 g, 2.534 mmol). The solution was stirred and purged with nitrogen for approximately 15 minutes, then tetrakis(triphenylphosphine)palladium(0) (0.2157 g, 0.1866 mmol) was added. The mixture was heated to reflux at 85° C. for 24 hours. During the 24 hours, a precipitate had formed. The reaction was allowed to cool to room temperature. The precipitate was isolated by vacuum filtration, and dried under high vacuum, for about an hour, to afford a crude protected ligand as an off white solid. The ligand was dissolved in a mixture of tetrahydrofuran (100 mL) and methanol (100 mL), and then heated to 60° C. At this time, the ligand was not completely dissolved. To the mixture, was added PTSA (0.6679 g, 3.511 mmol), until the mixture became acidic according to pH paper. To the reaction, was added chloroform (30 mL) to help dissolve the ligand. At this time, the ligand still was not completely dissolved. While stirring overnight, the ligand eventually completely dissolved. After stirring overnight, the ligand was analyzed by TLC for completion. The TLC analysis showed a shift in the location of the ligand, which meant the deprotection was complete. The ligand was concentrated by rotary evaporation, to afford an off white solid, and was analyzed by $^1$H NMR. The ligand was dissolved in chloroform, and silica gel was added. The slurry was concentrated by rotary evaporation, to afford a dry powdery mixture. The powdery mixture was loaded onto an ISCO COMBIFLASH system, which was run using a "330 g Grace column" and a gradient of 2-5% ethyl acetate in hexanes, until the product eluded. The fractions were analyzed by TLC. The pure fractions were combined, and concentrated by rotary evaporation, to afford the product as an off white solid. To remove traces of ethyl acetate, the solid was dissolved in dichloromethane, and concentrated by rotary evaporation, to afford an off white solid (repeated twice). The solid was dried under high vacuum to afford 2.48 g (74.4%). $^1$H NMR (400 MHz, CDCl$_3$) δ 8.21 (d, J=1.9 Hz, 2H), 8.20 (d, J=2.0 Hz, 2H), 7.37-7.35 (m, 4H), 7.31 (dd, J=8.6, 1.9 Hz, 2H), 7.23 (d, J=2.4 Hz, 2H), 7.19-7.17 (m, 3H), 7.00 (d, J=8.6 Hz, 2H), 6.97 (d, J=8.7 Hz, 2H), 6.94-6.91 (m, 2H), 6.88 (dd, J=8.7, 3.1 Hz, 2H), 6.31 (td, J=8.5, 3.1 Hz, 2H), 5.58-5.44 (m, 2H), 5.11 (s, 2H), 3.68-3.58 (m, 2H), 3.57-3.46 (m, 2H), 2.47 (d, J=7.8 Hz, 2H), 2.25-2.16 (broad m, 1H), 1.69 (s, 4H), 1.45 (s, 18H), 1.42 (s, 18H), 1.35 (s, 6H), 1.33 (s, 6H), 0.76 (s, 18H). $^{19}$F NMR (376 MHz, CDCl$_3$) δ −123.58--123.63 (broad m). HRMS (ESI, M+NH$_4$): (m/z) calcd for C$_{90}$H$_{110}$F$_2$N$_3$O$_4$ 1335.846, found 1335.848.

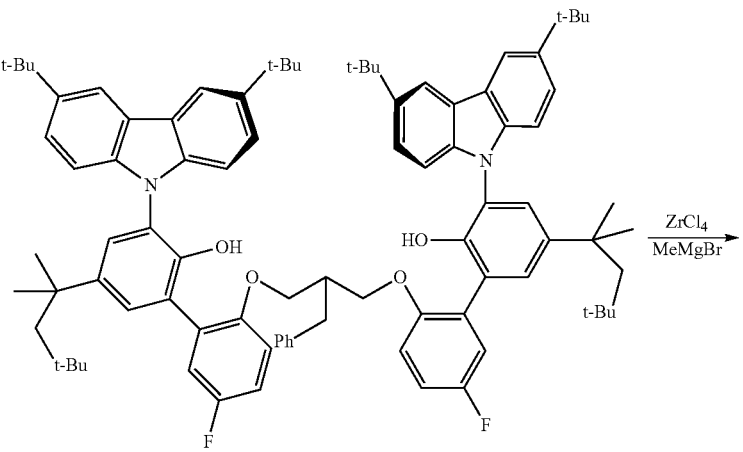

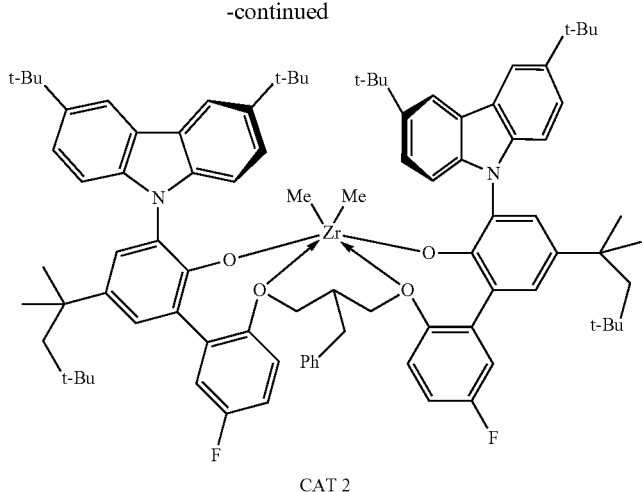

CAT 2

Preparation of CAT 2

To a mixture of the ligand (0.416 g, 0.32 mmol) and ZrCl$_4$ (0.070 g, 0.32 mmol) suspended in toluene (8 mL), was added 3M diethyl ether solution of MeMgBr (0.44 mL, 1.32 mmol). The suspension became black within 5 minutes. After stirring for 1.5 hours, at ambient temperature, the solvent was removed under reduced pressure. To the residue, was added hexane (20 mL), and resulting suspension was stirred for 10 minutes, and then filtered, giving a colorless solution. Solvent was removed under reduced pressure, leaving 0.363 mg (79.8%.) of product. $^1$H NMR (400 MHz, Benzene-d$_6$) δ 8.59 (t, J=1.3 Hz, 1H), 8.56-8.50 (m, 1H), 8.38 (dd, J=2.0, 0.7 Hz, 1H), 8.36 (dd, J=2.0, 0.7 Hz, 1H), 7.70 (d, J=2.5 Hz, 1H), 7.68-7.62 (m, 3H), 7.62 (dd, J=5.7, 0.6 Hz, 1H), 7.60 (dd, J=5.7, 0.6 Hz, 1H), 7.45 (dd, J=4.2, 1.9 Hz, 1H), 7.43 (dd, J=4.2, 1.9 Hz, 1H), 7.39-7.35 (m, 2H), 7.33 (d, J=2.5 Hz, 2H), 7.10-7.04 (m, 2H), 7.04-6.99 (m, 3H), 6.66-6.61 (m, 2H), 6.61-6.52 (m, 2H), 5.02 (ddd, J=10.5, 8.9, 4.8 Hz, 2H), 4.06 (dd, J=11.1, 9.3 Hz, 1H), 3.96 (dd, J=10.0, 4.1 Hz, 1H), 3.28-3.16 (m, 2H), 1.92-1.79 (m, 2H), 1.71-1.61 (m, 1H), 1.61-1.57 (m, 4H), 1.51 (s, 9H), 1.46 (s, 9H), 1.31 (s, 6H), 1.29 (s, 18H), 1.26 (s, 3H), 1.23 (s, 3H), 0.82 (s, 9H), 0.80 (s, 9H), −0.75 (s, 3H), −0.83 (s, 3H). $^{13}$C NMR (101 MHz, Benzene-d$_6$) δ 160.08 (d, J=246.1 Hz), 159.97 (d, J=245.7 Hz), 154.10, 154.07, 151.32 (d, J=2.5 Hz), 150.80 (d, J=2.5 Hz), 142.77, 142.66, 142.42, 142.28, 141.23, 140.97, 140.06, 140.03, 139.67, 139.59, 137.34, 134.39 (d, J=8.1 Hz), 134.02 (d, J=8.0 Hz), 129.39 (d, J=1.3 Hz), 129.24 (d, J=1.1 Hz), 128.58, 128.46, 128.08, 126.99, 126.92, 126.78, 124.86, 124.78, 124.68, 124.58, 123.73 (d, J=8.6 Hz), 123.47 (d, J=8.7 Hz), 122.99, 122.87, 122.53, 122.44, 117.97 (d, J=23.3 Hz), 117.79 (d, J=23.3 Hz), 116.69, 116.54, 115.92 (d, J=5.2 Hz), 115.82-115.49 (m), 112.20, 111.99, 108.77, 108.60, 79.48, 78.63, 56.91, 56.65, 42.84, 42.74, 40.18, 37.95, 34.89, 34.61, 34.54, 34.38, 32.19, 32.00, 31.96, 31.86, 31.75, 31.68, 31.66, 31.13, 31.05. $^{19}$F NMR (376 MHz, Benzene-d$_6$) δ −114.91-−115.10 (m), −115.28-−115.43 (m).

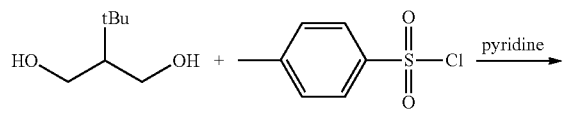

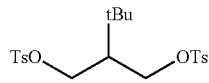

Preparation of 2-(tert-butyl)propane-1,3-diyl bis(4-methylbenzenesulfonate)

In a round bottomed flask, under nitrogen atmosphere, a solution of 2-(tert-butyl)propane-1,3-diol (5.000 g, 37.821 mmol), in anhydrous pyridine (12 mL), was added, dropwise, over the period of 2 hours, to a solution of p-toluenesulfonylchloride (17.323 g, 90.772 mmol), in anhydrous pyridine (50 mL), that was cooled to 0° C. The reaction was stirred for an additional 4 hours, placed in the freezer overnight, and then poured into 500 mL of ice water. The solid product was collected by filtration, washed with water, dilute sulfuric acid (10%), dilute sodium carbonate (1 M), and again with water. This wet product was recrystallized from ether, and dried to afford 11.15 g (66.9%). $^1$H NMR (400 MHz, CDCl$_3$) δ 7.67 (d, J=8.3 Hz, 4H), 7.28 (d, J=8.1 Hz, 4H), 4.07 (dd, J=10.1, 3.9 Hz, 2H), 3.98 (dd, J=10.1, 6.3 Hz, 2H), 2.37 (s, 6H), 1.62 (tt, J=6.3, 3.9 Hz, 1H), 0.79 (s, 9H). $^{13}$C NMR (101 MHz, CDCl$_3$) δ 144.82, 132.26, 129.75, 127.61, 66.97, 46.71, 31.74, 27.94, 21.41.

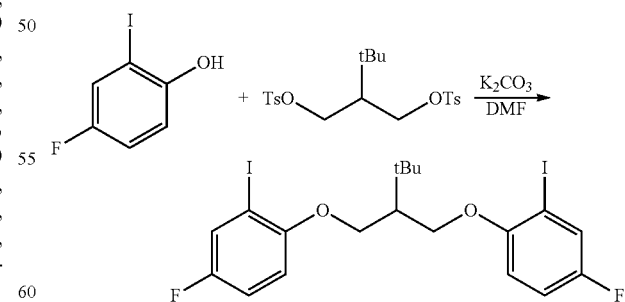

Preparation of 4,4'-((2-(tert-butyl)propane-1,3-diyl)bis(oxy))bis(1-fluoro-3-iodobenzene To a round-bottomed flask, under nitrogen atmosphere, was added 4-fluoro-2-iodophenol (6.000 g, 25.21 mmol), potassium carbonate (6.968 g, 50.42 mmol), 2-(tert-butyl) propane-1,3-diyl bis(4-methylbenzenesulfonate) (5.552 g, 12.605 mmol) and N,N-dimethylforamide (100 mL). The reaction was heated for 60 minutes, at 100° C., and then allowed to cool to room temperature. The mixture was concentrated to dryness, and the residue was taken up in 50/50 methylene chloride/water mixture, and extracted into methylene chloride. The organic phases were washed with 2 N sodium hydroxide, brine, water, and dried over magnesium sulfate, filtered and concentrated, to afford 4.73 g (65.6%) of the product, as a slightly yellow, very viscous oil. $^1$H NMR (400 MHz, CDCl$_3$, δ 7.45 (dd, J=7.6, 3.0 Hz, 2H), 7.01 (ddd, J=9.0, 7.8, 3.0 Hz, 2H), 6.83 (dd, J=9.0, 4.6 Hz, 2H), 4.35-4.26 (m, 4H), 2.08 (tt, J=5.8, 4.4 Hz, 1H), 1.16 (s, 9H). $^{13}$C NMR (101 MHz, CDCl$_3$) δ 157.86, 155.44, 154.24, 154.22, 126.04, 125.79, 115.63, 115.39, 112.30, 112.22, 85.80, 85.71, 67.40, 47.69, 31.92, 29.09. $^{19}$F NMR (376 MHz, CDCl$_3$) δ −122.51 (td, J=7.7, 4.8 Hz).

Preparation of 6',6'''-((2-(tert-butyl)propane-1,3-diyl)bis(oxy))bis(3-(3,6-di-tert-butyl-9H-carbazol-9-yl)-3'-fluoro-5-(2,4,4-trimethylpentan-2-yl)-[1,1'-biphenyl]-2-ol)

To 1,2-dimethoxyethane (69 mL), was added 3,6-di-tert-butyl-9-(2-((tetrahydro-2H-pyran-2-yl)oxy)-3-(4,4,5,5-tetramethyl-1,3,2-dioxaborolan-2-yl)-5-(2,4,4-trimethylpentan-2-yl)phenyl)-9H-carbazole (4.00 g, 5.650 mmol), 4,4'-((2-(tert-butyl)propane-1,3-diyl)bis(oxy))bis(1-fluoro-3-iodobenzene) (1.583 g, 2.684 mmol), a solution of sodium hydroxide (0.678 g, 16.950) in 16 mL of water, and tetrahydrofuran (40 mL). The reaction mixture was sparged with nitrogen for about 15 minutes. Then tetrakis(triphenylphosphine)palladium(0) (0.130 g, 0.1130 mmol) was added, and the mixture was heated to 85° C. overnight. $^{19}$F NMR was used to determine reaction completion. The reaction was allowed to cool to room temperature. The reaction was concentrated, with the residue taken up in methylene chloride (200 mL), washed with brine (200 mL), dried over anhydrous magnesium sulfate, filtered through a pad of silica gel, and concentrated, to afford the crude protected ligand. To the crude ligand, was added tetrahydro-furan (50

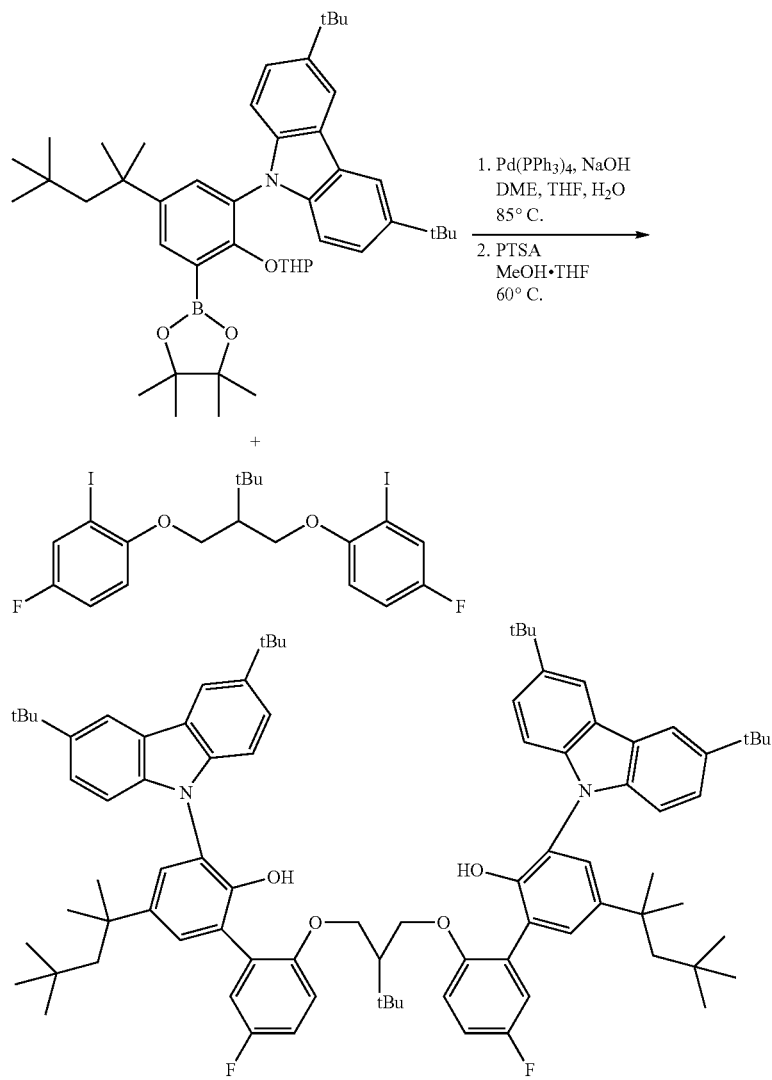

mL), methanol (50 mL), and approximately 100 mg of p-toluenesulfonic acid monohydrate. The solution was heated to 60° C. overnight, then allowed to cool to room temperature, and concentrated. The crude ligand was taken up in methylene chloride (100 mL), washed with brine (100 mL), dried over anhydrous magnesium sulfate, filtered through a pad of silica gel, and then concentrated, to afford the ligand as a brown crystalline powder. The solid was purified by column chromatography on an ISCO Combi flash instrument, using a 330 g Grace Reveleris catridge, and eluting with a "20-30% methylene chloride in hexanes gradient," to afford 2.02 g (58.6%) of product as white crystalline solid. $^1$H NMR (400 MHz, CDCl$_3$) δ 8.36 (t, J=1.5 Hz, 4H), 7.54 (ddd, J=13.5, 8.6, 1.9 Hz, 4H), 7.47 (d, J=2.4 Hz, 2H), 7.28 (d, J=2.4 Hz, 2H), 7.15 (d, J=8.6 Hz, 2H), 7.08 (d, J=8.6 Hz, 2H), 6.94 (dd, J=8.7, 3.2 Hz, 2H), 6.40-6.30 (m, 2H), 5.68-5.55 (m, 2H), 5.21 (s, 2H), 3.89-3.76 (m, 4H), 1.78 (s, 4H), 1.76-1.68 (m, 1H), 1.58 (s, 18H), 1.58 (s, 18H), 1.44 (s, 6H), 1.41 (s, 6H), 0.88 (s, 9H), 0.87 (s, 18H). $^{13}$C NMR (101 MHz, CDCl$_3$) δ 157.91, 155.53, 151.14, 151.12, 147.84, 142.79, 142.77, 139.98, 139.94, 129.10, 127.57, 127.49, 127.26, 126.31, 123.96, 123.59, 123.50, 123.36, 123.28, 117.97, 117.73, 116.29, 116.21, 115.32, 115.09, 112.00, 111.91, 109.39, 109.24, 65.77, 56.98, 47.47, 38.15, 34.79, 34.77, 32.42, 32.10, 31.91, 31.77, 31.65, 31.55, 28.79. $^{19}$F NMR (376 MHz, CDCl$_3$) δ −123.77 (broad s). HRMS (ESI, M+NH$_4^+$): (m/z) calcd for C$_{87}$H$_{112}$F$_2$N$_3$O$_4$ 1300.862, found 1300.861.

Preparation of CAT3

In the glovebox, 0.21 mL of MeMgBr (3.0 M in ether, 0.64 mmol) was combined with 10 mL of toluene, and cooled to −30° C. To this, was added ZrCl$_4$ (0.035 g, 0.15 mmol), and the mixture was allowed to stir for 5 minutes, during which time, it turned gray/black. At this point, the ligand (0.20 g, 0.15 mmol) was added slowly as a solid. The cooling was removed, and the mixture was allowed to warm to room temperature. After stirring overnight, the mixture was filtered through a 0.45 micron PTFE syringe filter. The filtrate was dried in vacuo. The residues were dissolved in 5 mL of a 50/50 toluene/hexanes combination, and filtered through a 0.45 micron PTFE syringe filter, and the volatiles removed in vacuo. Yield: 0.11 g (50%). An NMR sample was prepared in C$_6$D6. $^1$H NMR (C$_6$D6, 400 MHz, RT): 8.60 ppm (m, 2H), 8.38 (dd, J=6.9 Hz, 1.9 Hz, 2H), 7.64 (m, 8H), 7.45 (ddd, J=8.8 Hz, 5.5 Hz, 1.9 Hz, 2H), 7.25 (dd, J=10.4 Hz, 2.5 Hz, 2H), 6.99 (ddd, J=8.6 Hz, 5.2 Hz, 3.1 Hz), 6.58 (dddd, J=30.8 Hz, 8.9 Hz, 7.3 Hz, 3.2 Hz, 2H), 5.23 (dd, J=8.9 Hz, 4.8 Hz, 1H), 5.02 (dd, J=8.9 Hz, 4.9 Hz, 1H), 4.24 (dd, J=11.5 Hz, 10.0 Hz, 1H), 4.04 (dd, J=9.4 Hz, 5.9 Hz, 1H), 3.47 (dd, J=11.5 Hz, 3.0 Hz, 1H), 3.31 (dd, J=9.5 Hz, 7.7 Hz, 1H), 1.60 (m, 5H), 1.50 (s, 9H), 1.46 (s, 9H), 1.30 (s, 18H), 0.90 (s, 3H), 0.88 (s, 6H), 0.86 (s, 3H), 0.85 (s, 9H), 0.82 (s, 9H), 0.29 (s, 9H), −0.68 (s, 3H), −0.86 (s, 3H).

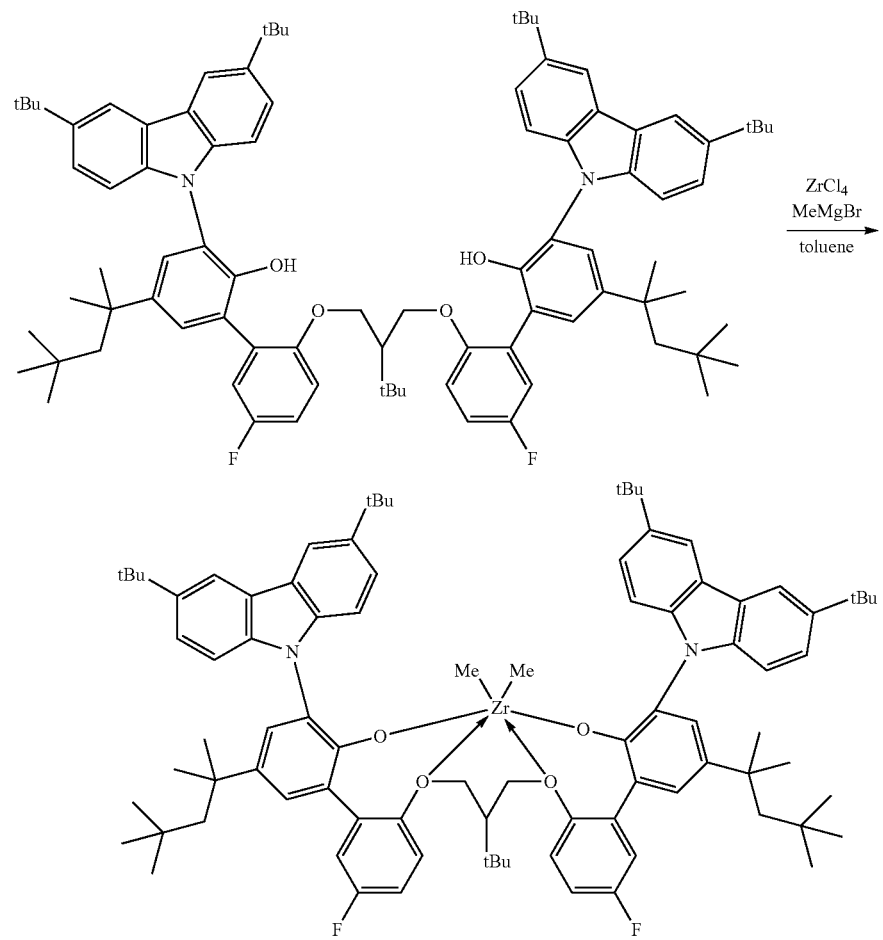

CAT 3

$^{13}C\text{-}\{^1H\}$NMR (C$_6$D6, 100 MHz, RT): 160.5 ppm (d, J=246 Hz), 160.4 (d, J=246 Hz), 154.4, 154.1, 151.9 (d, J=2.4 Hz), 150.8 (d, J=2.4 Hz), 143.0, 142.8, 142.8, 141.6, 141.4, 140.5, 140.3, 140.0, 135.2 (d, J=7.7 Hz), 134.7 (d, J=7.7 Hz), 130.0, 129.5, 129.3, 128.5, 127.6, 127.5, 127.0, 125.4, 125.1 (d, J=8.7 Hz), 125.1, 125.0, 125.0, 124.0 (d, J=8.7 Hz), 123.2, 122.9, 122.7, 118.4 (d, J=8.8 Hz), 118.2 (d, J=8.8 Hz), 117.2, 117.0, 116.3 (d, J=23.0 Hz), 115.9 (d, J=23.0 Hz), 115.9, 115.9, 112.7, 112.5, 108.9, 108.8, 79.2, 77.9, 56.7, 56.7, 47.9, 43.3, 42.6, 38.3, 38.2, 35.0, 34.9, 34.7, 32.5, 32.5, 32.3, 32.3, 32.2, 32.1, 32.0, 31.9, 31.5, 31.2, 27.0, 23.0, 14.3. $^{19}F\text{-}\{^1H\}$ NMR (C$_6$D6, 376 MHz, RT): −114.5–115.3 ppm (m).

Transition Metal Complex Structures

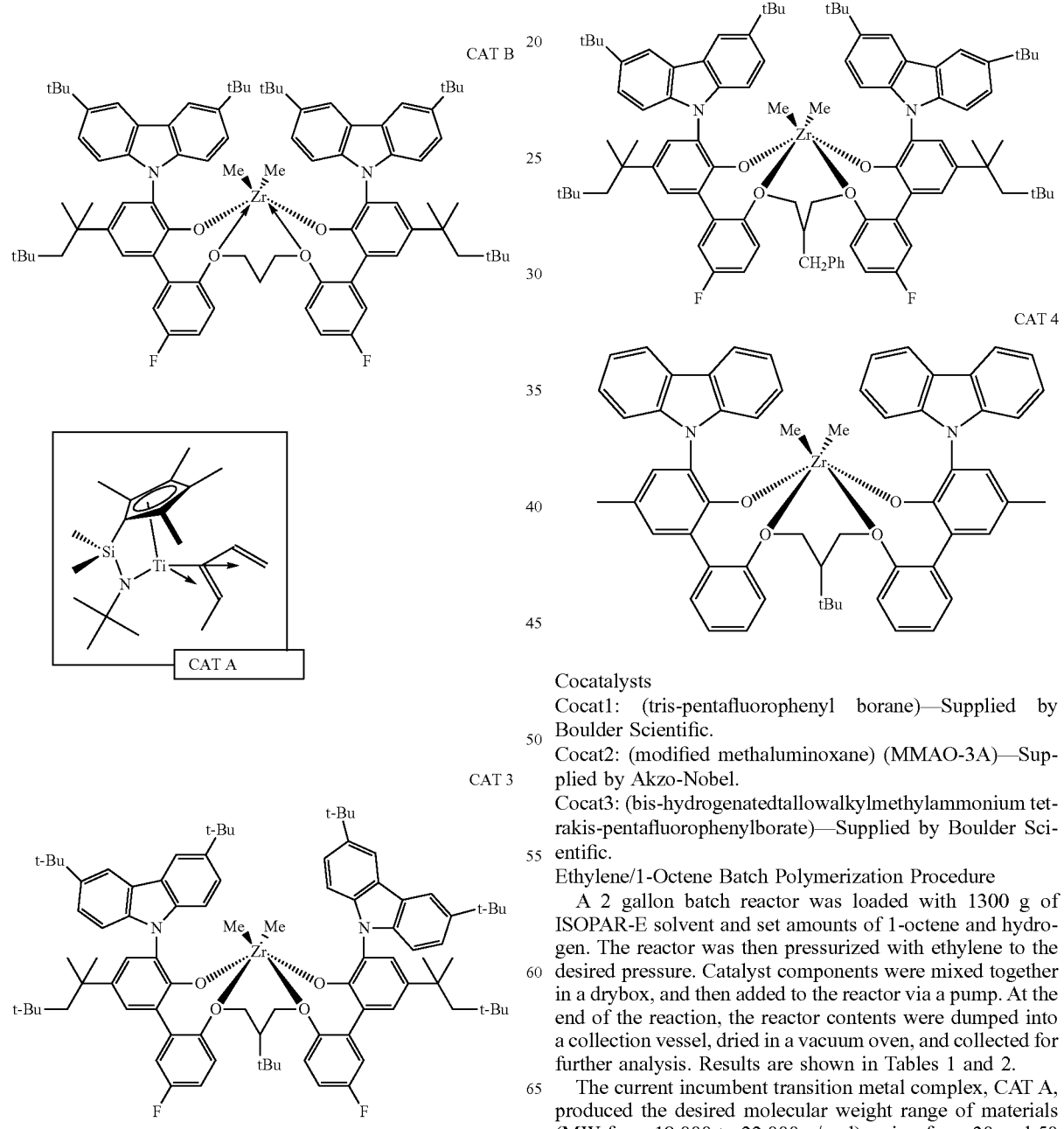

Cocatalysts

Cocat1: (tris-pentafluorophenyl borane)—Supplied by Boulder Scientific.

Cocat2: (modified methaluminoxane) (MMAO-3A)—Supplied by Akzo-Nobel.

Cocat3: (bis-hydrogenatedtallowalkylmethylammonium tetrakis-pentafluorophenylborate)—Supplied by Boulder Scientific.

Ethylene/1-Octene Batch Polymerization Procedure

A 2 gallon batch reactor was loaded with 1300 g of ISOPAR-E solvent and set amounts of 1-octene and hydrogen. The reactor was then pressurized with ethylene to the desired pressure. Catalyst components were mixed together in a drybox, and then added to the reactor via a pump. At the end of the reaction, the reactor contents were dumped into a collection vessel, dried in a vacuum oven, and collected for further analysis. Results are shown in Tables 1 and 2.

The current incumbent transition metal complex, CAT A, produced the desired molecular weight range of materials (MW from 18,000 to 22,000 g/mol), using from 30 and 50 mmole of hydrogen addition, and at relatively low polymerization temperatures (120-130° C.). A unsubstituted C3-bridged bis-phenyl-phenoxy catalyst, CAT B, required 200 to 300 mmole of hydrogen to make the same molecular weight range at elevated temperatures.

For the four inventive transition metal complexes (CAT 1, CAT 2, CAT 3 and CAT 4), the desired low molecular weights, and low densities, were achieved using from 0 to 80 mmole hydrogen addition, and at significantly higher temperatures (175-179° C.).

Continuous Polymerizations

All the continuous experiments were performed in a liquid-full, 5 liter, jacketed stirred-tank reactor, rated for 50 bar and 250° C. Ethylene, solvent, hydrogen and octene were mixed in a feed line, and fed to the bottom of the reactor, in a continuous fashion, in the amounts listed in Tables 3A and 4A. The catalysts and cocatalyst components were pumped into the reactor through separate lines. The amounts of catalyst components added, were controlled to convert 92% of the ethylene fed to the reactor, as measured

TABLE 1

(Comparative Transition Metal Complexes, CAT A and CAT B)

| run | Temp (° C.) | Metal Complex | Cocat. | ISOPAR (g) | C2 pressure (PSI) | Hydrogen (mmol) | Octene (g) | Efficiency gPE/gM | Mw g/mol | Mn g/mol | Mw/Mn | Density g/cc |
|---|---|---|---|---|---|---|---|---|---|---|---|---|
| 1 | 128.2 | CAT A | Cocat1/Cocat2 | 1331 | 321.5 | 30 | 280.5 | 249,992 | 23,678 | 11,857 | 2.00 | |
| 2 | 129.6 | CAT A | Cocat1/Cocat2 | 1338 | 324 | 40 | 280.1 | 236,677 | 20,245 | 10,400 | 1.95 | 0.8776 |
| 3 | 129.4 | CAT A | Cocat1/Cocat2 | 1339 | 321.5 | 50 | 280.2 | 204,032 | 16,345 | 8,243 | 1.98 | |
| 4 | 129 | CAT A | Cocat1/Cocat2 | 1333.5 | 322.1 | 60.1 | 281.1 | 166,689 | 14,615 | 7,155 | 2.04 | |
| 5a | 171.3 | CAT B | Cocat3/Cocat2 | 1335.8 | 455.7 | 200.1 | 371.4 | 1,769,736 | 20,921 | 9,725 | 2.15 | |
| 6a | 171.5 | CAT B | Cocat3/Cocat2 | 1337.3 | 461.5 | 300.1 | 370 | 1,667,313 | 16,584 | 7,293 | 2.27 | 0.879 |
| 7a | 170 | CAT B | Cocat3/Cocat2 | 1330 | 430 | 400 | 370 | 1,583,580 | 13,264 | 5,689 | 2.33 | |

TABLE 2

(Inventive Transition Metal Complexes, CAT 1, CAT 2, CAT 3, CAT 4)

| run | Temp. (C.) | Metal Complex | Cocat | ISOPAR (g) | C2 pressure (PSI) | Hydrogen (mmol) | Octene (g) | Efficiency gPE/gM | Mw g/mol | Mn g/mol | Density g/cc |
|---|---|---|---|---|---|---|---|---|---|---|---|
| 43 | 177.5 | CAT 1 | Cocat3/Cocat2 | 1332.1 | 448.7 | 0 | 331.4 | 3,014,226 | 21,836 | 10,986 | |
| 44 | 176.8 | CAT 1 | Cocat3/Cocat2 | 1335.3 | 453.8 | 20 | 331.7 | 1,961,136 | 20,900 | 10,598 | |
| 45 | 178.1 | CAT 1 | Cocat3/Cocat2 | 1330.2 | 455.7 | 40 | 332.1 | 1,764,375 | 19,449 | 9770 | 0.8852 |
| 46 | 177.7 | CAT 1 | Cocat3/Cocat2 | 1331.2 | 451.3 | 80.1 | 330.9 | 1,471,411 | 17,497 | 9,005 | |
| 51 | 175.9 | CAT 2 | Cocat3/Cocat2 | 1336.5 | 451.3 | 0 | 330.8 | 463,527 | 18,223 | 9,451 | |
| 52 | 177.9 | CAT 2 | Cocat3/Cocat2 | 1338.6 | 448.7 | 20 | 330.2 | 464,508 | 17,120 | 8,630 | |
| 53 | 176.7 | CAT 2 | Cocat3/Cocat2 | 1338.1 | 437.3 | 40 | 330.4 | 600,191 | 15,891 | 7,677 | 0.8772 |
| 54 | 176.5 | CAT 2 | Cocat3/Cocat2 | 1332.6 | 437.9 | 80.1 | 330.8 | 464,436 | 14,018 | 6,842 | |
| 59 | 175.7 | CAT 3 | Cocat3/Cocat2 | 1339.1 | 449.6 | 0 | 330.7 | 541,024 | 26,122 | 12,375 | |
| 60 | 177.9 | CAT 3 | Cocat3/Cocat2 | 1330.8 | 446.4 | 20 | 330.2 | 576,539 | 23,705 | 11,774 | |
| 61 | 176.1 | CAT 3 | Cocat3/Cocat2 | 1334.6 | 440.1 | 40 | 330.1 | 503,913 | 20,741 | 10,356 | 0.8743 |
| 62 | 178.2 | CAT3 | Cocat3/Cocat2 | 1334.4 | 447.7 | 80.1 | 330.1 | 523,351 | 17,365 | 8,511 | |
| 67 | 177.2 | CAT 4 | Cocat3/Cocat2 | 1337 | 476.1 | 0 | 331.1 | 1,097,467 | 24,774 | 12,641 | |
| 68 | 178 | CAT 4 | Cocat3/Cocat2 | 1332.5 | 482.5 | 20 | 330.2 | 1,028,438 | 22,431 | 11,742 | |
| 69 | 174.7 | CAT 4 | Cocat3/Cocat2 | 1338.1 | 440.4 | 40 | 330.1 | 828,801 | 20,473 | 9,956 | 0.8746 |
| 70 | 178 | CAT 4 | Cocat3/Cocat2 | 1334.5 | 449.4 | 80.1 | 330.1 | 746,047 | 17,062 | 8,035 | | by FTIR on the reactor exit line. The reactor temperature was controlled, to the desired set point, by an external jacket heated with hot oil. Upon exiting the reactor, the solvent/polymer mixture was preheated, before it entered the devolatilizers, in which the solvent and non-converted monomers were removed. The final dry polymer was collected in pans, and analyzed for polymer density, viscosity and molecular weight. See Tables 3B and 4B for polymer properties.

TABLE 3A (Comparative Transition Metal Complexes, CAT A and CAT B)

| Temp. (° C.) | Metal Complex | cocatalysts | ISOPAR-E (kg/hr) | C2 (kg/hr) | Hydrogen (ml/min)* | Octene (kg/hr) | Efficiency (gPE/gmetal) |
|---|---|---|---|---|---|---|---|
| 130 | CAT A | Cocat1/Cocat2 | 18.9 | 2.35 | 55 | 2.4 | 370,000 |
| 130 | CAT A | Cocat1/Cocat2 | 18.95 | 2.35 | 27 | 2.2 | 390,000 |
| 170 | CAT B | Cocat3/Cocat2 | 18.2 | 2.35 | 150 | 2.9 | 3,010,000 |
| 190 | CAT B | Cocat3/Cocat2 | 17.9 | 2.35 | 135 | 3.1 | 1,320,000 |
| 170 | CAT B | Cocat3/Cocat2 | 17.8 | 2.35 | 210 | 3.4 | 5,680,000 |
| 190 | CAT B | Cocat3/Cocat2 | 17.5 | 2.35 | 170 | 3.6 | 3,840,000 |

*Standard ml/min

TABLE 3B (Comparative Transition Metal Complexes, CAT A and CAT B)

| Temp. (° C.) | Metal Complex | COCAT. | Viscosity (cP) | Density g/cc | Mw (g/mol) | Mn (g/mol) | MWD |
|---|---|---|---|---|---|---|---|
| 130 | CAT A | Cocat1/Cocat2 | 8,250 | 0.8712 | 19,022 | 7,663 | 2.48 |
| 130 | CAT A | Cocat1/Cocat2 | 14,222 | 0.8741 | 21,238 | 8,518 | 2.49 |
| 170 | CAT B | Cocat3/Cocat2 | 20,000 | 0.8758 | 24,474 | 8,617 | 2.84 |
| 190 | CAT B | Cocat3/Cocat2 | 19,631 | 0.8759 | 28,988 | 8,722 | 3.32 |
| 170 | CAT B | Cocat3/Cocat2 | 8,540 | 0.8705 | 19,980 | 8,020 | 2.49 |
| 190 | CAT B | Cocat3/Cocat2 | 8,702 | 0.8702 | 20,001 | 6,800 | 2.94 |

TABLE 4A (Inventive Transition Metal Complexes, CAT 1, CAT 3)

| Temp. (° C.) | Metal Complex | cocatalysts | ISOPAR-E (kg/hr) | C2 (kg/hr) | Hydrogen (ml/min)* | Octene (kg/hr) | Efficiency (gPE/gmetal) |
|---|---|---|---|---|---|---|---|
| 190 | CAT 1 | Cocat3/Cocat2 | 17.7 | 2.35 | 0 | 2.9 | 4,950,000 |
| 170 | CAT 1 | Cocat3/Cocat2 | 18.2 | 2.35 | 30.6 | 2.65 | 9,030,000 |
| 170 | CAT 1 | Cocat3/Cocat2 | 17.5 | 2.35 | 52 | 2.95 | 8,530,000 |
| 190 | CAT 1 | Cocat3/Cocat2 | 17.3 | 2.35 | 10 | 3.15 | 4,260,000 |
| 190 | CAT 3 | Cocat3/Cocat2 | 18.15 | 2.35 | 50 | 2.85 | 3,370,000 |
| 170 | CAT 3 | Cocat3/Cocat2 | 17.8 | 2.35 | 85 | 2.65 | 4,000,000 |
| 170 | CAT 3 | Cocat3/Cocat2 | 18 | 2.35 | 60 | 2.42 | 5,330,000 |
| 190 | CAT 3 | Cocat3/Cocat2 | 17.83 | 2.35 | 30 | 2.58 | 3,550,000 |

*Standard ml/min

TABLE 4B (Inventive Transition Metal Complexes, CAT 1, CAT 3)

| Temp. (C.) | Metal Complex | cocatalysts | Viscosity (cP) | Density g/cc | Mw (g/mol) | Mn (g/mol) | MWD |
|---|---|---|---|---|---|---|---|
| 190 | CAT 1 | Cocat3/Cocat2 | 16,000 | 0.8746 | 23,406 | 7,388 | 3.17 |
| 170 | CAT 1 | Cocat3/Cocat2 | 17,900 | 0.8746 | 24,169 | 7,511 | 3.22 |
| 170 | CAT 1 | Cocat3/Cocat2 | 8230 | 0.8692 | 20,542 | 6,554 | 3.13 |
| 190 | CAT 1 | Cocat3/Cocat2 | 8550 | 0.8695 | 21,216 | 6,371 | 3.33 |
| 190 | CAT 3 | Cocat3/Cocat2 | 8100 | 0.8699 | 20,765 | 7,021 | 2.96 |
| 170 | CAT 3 | Cocat3/Cocat2 | 7800 | 0.8702 | 20,416 | 8,096 | 2.52 |
| 170 | CAT 3 | Cocat3/Cocat2 | 17,600 | 0.8733 | 23,540 | 9,058 | 2.60 |
| 190 | CAT 3 | Cocat3/Cocat2 | 16,200 | 0.8737 | 23,435 | 8,064 | 2.91 |

Comparative polymerizations using CAT A were capable of producing low molecular weight ethylene-based polymers (for example, ≤20,000 cP at 177° C.), and low densities (e.g., <0.90 g/cc), using reasonable levels of hydrogen and comonomer, but only at low reactor temperatures (<150° C.). At elevated temperatures, the catalyst efficiency drops too low to be commercially feasible. Comparative polymerizations using CAT B, which contains no alkyl substituents on the C3 bridge, were capable of producing the desired low molecular weight ethylene-based polymers, at elevated temperature with good catalyst efficiency; however significantly higher levels of hydrogen were required, as compared to the inventive polymerizations. In some case, the level of hydrogen needed was greater than five times that needed for a corresponding inventive polymerization.

The inventive polymerizations using CAT 1 or CAT 3 were able to produce the desired low molecular weight ethylene-based polymers at high reactor temperatures, and with excellent catalyst efficiency. Very reasonable levels of hydrogen and octene were required, similar to those needed for the comparative polymerizations using CAT A.

The invention claimed is:

1. A process to form an ethylene-based polymer, said process comprising polymerizing ethylene, and optionally at least one comonomer, in the presence of at least one molecular transition metal complex selected from Formula 1:

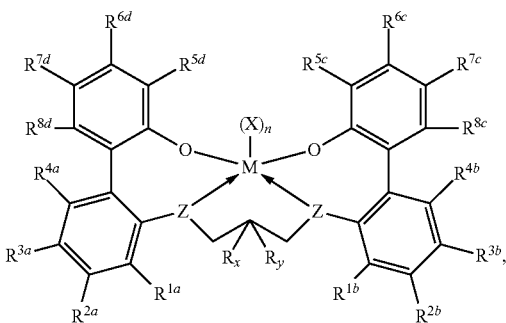

(Formula 1)

wherein M is titanium, zirconium, or hafnium, each independently being in a formal oxidation state of +2, +3, or +4;

n is an integer of from 0 to 3, wherein when n is 0, X is absent;

each X is independently a monodentate ligand that is neutral, monoanionic, or dianionic, or two X are taken together to form a bidentate ligand that is neutral, monoanionic, or dianionic;

X and n are selected such that the metal-ligand complex is neutral;

each Z moiety is, independently, —O—, —S—, —N[(C$_1$-C$_{40}$)hydrocarbyl]-, or —P[(C$_1$-C$_{40}$)hydrocarbyl]-;

R$_x$ is selected from the following: a substituted or unsubstituted (C$_1$-C$_{40}$)hydrocarbyl; a substituted or unsubstituted (C$_1$-C$_{40}$)heterohydrocarbyl; —Si(R$^C$)$_3$, —OSi(R$^C$)$_3$—Ge(R$^C$)$_3$, —P(R$^C$)$_2$, —N(R$^C$)$_2$, —OR$^C$, —SR$^C$, —NO$_2$, —CN, —CF$_3$, —OCF$_3$, —S(O)R$^C$, —S(O)$_2$R$^C$, —N=C(R$^C$)$_2$, —OC(O)R$^C$, —C(O)OR$^C$, —N(R)C(O)R$^C$, —C(O)N(R$^C$)$_2$, a halogen, or a hydrogen; and wherein each R$^C$ is independently a substituted or unsubstituted (C$_1$-C$_{30}$)hydrocarbyl, or a substituted or unsubstituted (C$_1$-C$_{30}$) heterohydrocarbyl;

R$_y$ is selected from the following: a substituted or unsubstituted (C$_1$-C$_{40}$)hydrocarbyl; a substituted or unsubstituted (C$_1$-C$_{40}$)heterohydrocarbyl; —Si(R$^C$)$_3$, —OSi(R$^C$)$_3$, —Ge(R$^C$)$_3$, —P(R$^C$)$_2$, —N(R$^C$)$_2$, —OR$^C$, —SR$^C$, —NO$_2$, —CN, —CF$_3$, —OCF$_3$, —S(O)R$^C$, —S(O)$_2$R$^C$, —N=C(R$^C$)$_2$, —OC(O)R$^C$, —C(O)OR$^C$, —N(R)C(O)R$^C$, —C(O)N(R$^C$)$_2$, a halogen, or a hydrogen; and wherein each R$^C$ is independently a substituted or unsubstituted (C$_1$-C$_{30}$)hydrocarbyl, or a substituted or unsubstituted (C$_1$-C$_{30}$) heterohydrocarbyl; and wherein, when Rx is hydrogen, Ry is not hydrogen, and when Ry is hydrogen, Rx is not hydrogen; and wherein Rx and Ry optionally form a ring structure; and wherein R$^{1a}$, R$^{2a}$, R$^{3a}$, R$^{4a}$, R$^{1b}$, R$^{2b}$, R$^{3b}$, R$^{4b}$, R$^{5c}$, R$^{6c}$, R$^{7c}$, R$^{8c}$, R$^{5d}$, R$^{6d}$, R$^{7d}$ and R$^{8d}$ are each, independently, selected from the following: a substituted or unsubstituted (C$_1$-C$_{40}$)-hydrocarbyl, a substituted or unsubstituted (C$_1$-C$_{40}$)heterohydrocarbyl, —Si(R$^C$)$_3$, —OSi(R$^C$)$_3$, —Ge(R$^C$)$_3$, —P(R$^C$)$_2$, —N(R$^C$)$_2$, —OR$^C$, —SR$^C$, —NO$_2$, —CN, —CF$_3$, —OCF$_3$, —S(O)R$^C$, —S(O)$_2$R$^C$, —N=C(R$^C$)$_2$, —OC(O)R$^C$, —C(O)OR$^C$, —N(R)C(O)R$^C$, —C(O)N(R$^C$)$_2$, a halogen, or a hydrogen; and wherein each R$^C$ is independently a substituted or unsubstituted (C$_1$-C$_{30}$)hydrocarbyl, or a substituted or unsubstituted (C$_1$-C$_{30}$) heterohydrocarbyl; and wherein, for Formula 1, one or more hydrogen atoms optionally be substituted with deuterium, and wherein, for Formula 1, two or more of R$^{1a}$, R$^{2a}$, R$^{3a}$, R$^{4a}$, R$^{1b}$, R$^{2b}$, R$^{3b}$, R$^{4b}$, R$^{5c}$, R$^{6c}$, R$^{7c}$, R$^{8c}$, R$^{5d}$, R$^{6d}$, R$^{7d}$ and R$^{8d}$ optionally form one or more ring structures.

2. The process of claim 1 wherein at least one of R$^{3a}$ or R$^{3b}$ is a halogen.

3. The process of claim 1, wherein Rx or Ry is hydrogen, and the other is a substituted or unsubstituted (C1-C40) hydrocarbyl.

4. The process of claim 3, wherein Rx or Ry is hydrogen, and the other is an unsubstituted (C1-C20) hydrocarbyl.

5. The process of claim 1, wherein each Z is —O— (oxygen atom).

6. The process of claim 1, wherein n is 2, and each X is independently an alkyl.

7. The process of claim 1, wherein R$^{5c}$ and R$^{5d}$ are each independently selected from the following: 1,2,3,4-tetrahydronaphthyl; anthracenyl; 1,2,3,4-tetrahydroanthracenyl; 1,2,3,4,5,6,7,8-octahydroanthracenyl; phenanthrenyl; 1,2,3,4,5,6,7,8-octahydrophenanthrenyl; 2,6-dimethylphenyl; 2,6-diisopropylphenyl; 3,5-di(tertiary-butyl)phenyl; 3,5-diphenylphenyl; 1-naphthyl; 2-methyl-1-naphthyl; 2-naphthyl; 1,2,3,4-tetra-hydronaphth-5-yl; 1,2,3,4-tetrahydronaphth-6-yl; anthracen-9-yl; 1,2,3,4-tetrahydro-anthracen-9-yl; 1,2,3,4,5,6,7,8-octahydroanthracen-9-yl; 1,2,3,4,5,6,7,8-octahydrophenanthren-9-yl; indolyl; indolinyl; quinolinyl; 1,2,3,4-tetrahydroquinolinyl; isoquinolinyl; 1,2,3,4-tetrahydroisoquinolinyl; carbazolyl; 1,2,3,4-tetrahydrocarbazolyl; 1,2,3,4,5,6,7,8-octahydrocarbazolyl; 3,6-di(tertiary-butyl)-carbazol-9-yl; 3,6-di(tertiary-octyl)-carbazol-9-yl; 3,6-diphenylcarbazol-9-yl; 3,6-bis(2,4,6-trimethylphenyl)-carbazol-9-yl; 2,7-di(tertiary-butyl)-carbazol-9-yl; 2,7-di(tertiary-octyl)-carbazol-9-yl; 2,7-diphenylcarbazol-9-yl; or 2,7-bis(2,4,6-trimethylphenyl)-carbazol-9-yl.

8. The process of claim 1, wherein R$^{7c}$ and R$^{7d}$ are each independently an alkyl.

9. The process of claim 1, wherein R$^{1a}$, R$^{2a}$, R$^{4a}$, R$^{1b}$, R$^{2b}$, R$^{4b}$, R$^{6c}$, R$^{8c}$, R$^{6d}$ and R$^{8d}$ are each hydrogen.

10. The process of claim 1, wherein the process is run at a polymerization temperature greater than, or equal to, 170° C.

11. The process of claim 1, wherein the ethylene-based polymer has a melt viscosity, at 177° C., less than, or equal to, 50,000 cP.

12. The process of claim 1, wherein the ethylene-based polymer is an ethylene/α-olefin copolymer.

13. The process of claim 1, wherein Formula 1 is selected from the following structures a) through dd):

a)
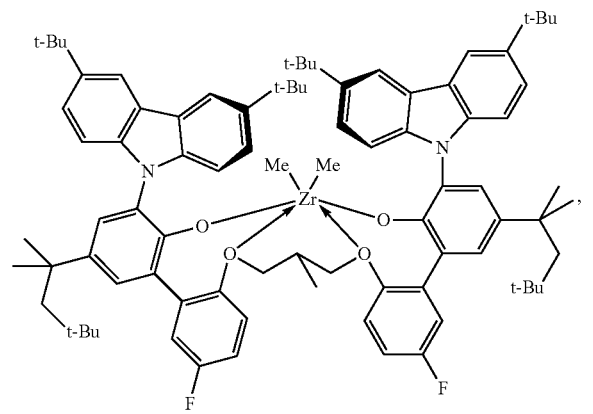

b)
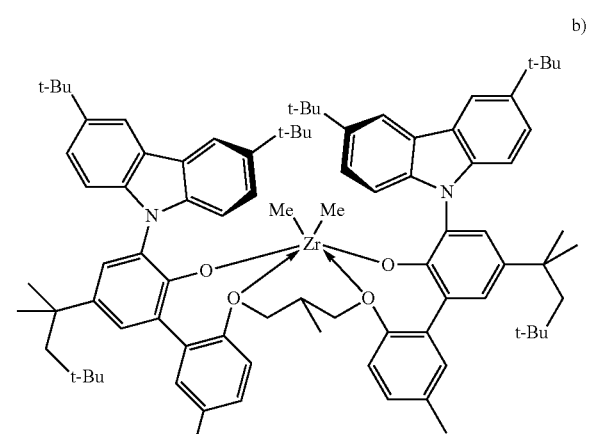

c)
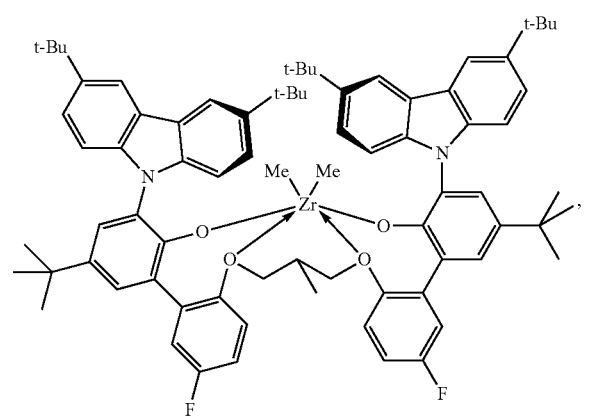

-continued d)
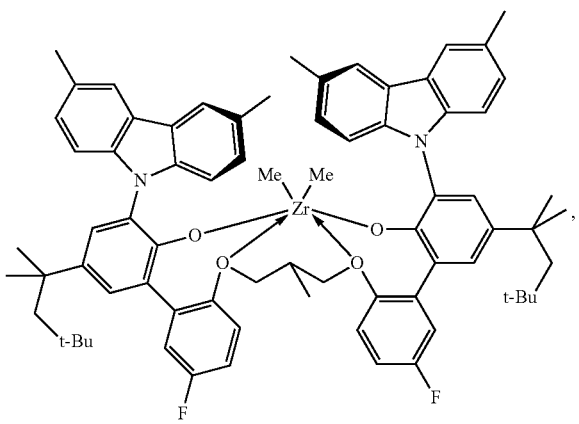

e)
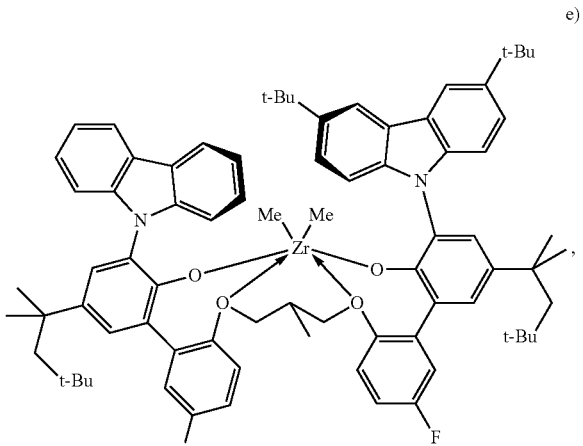

f)
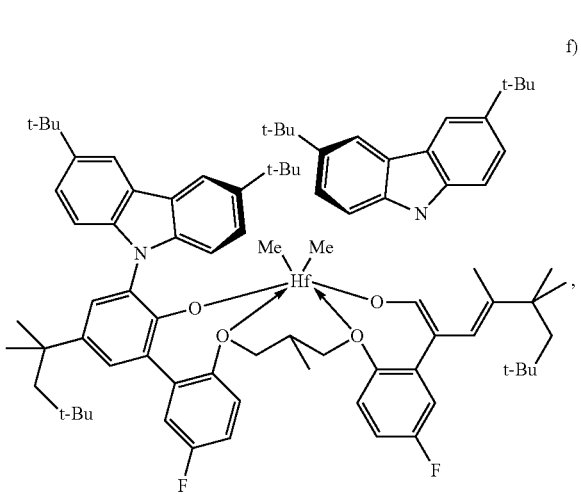

g)
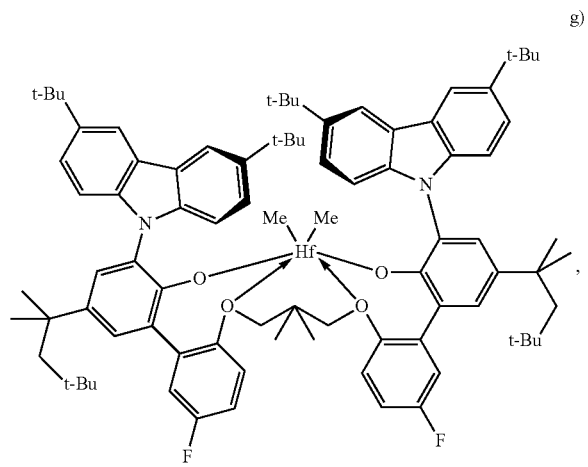
j)
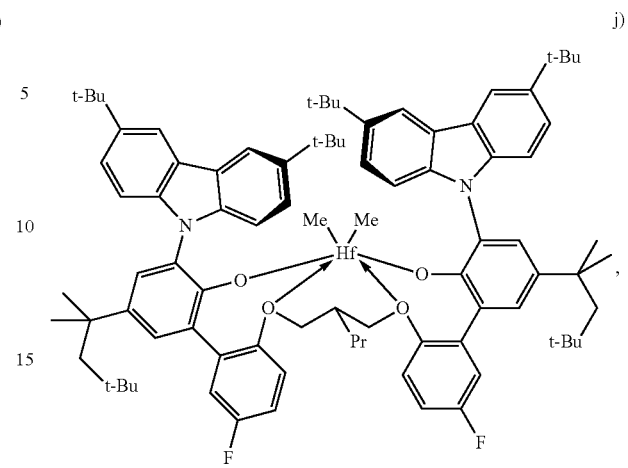
h)
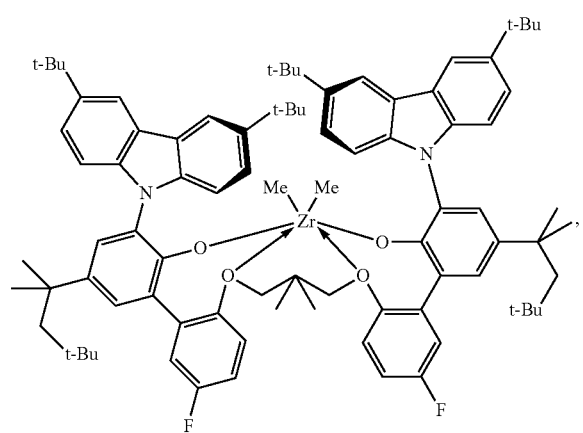
k)
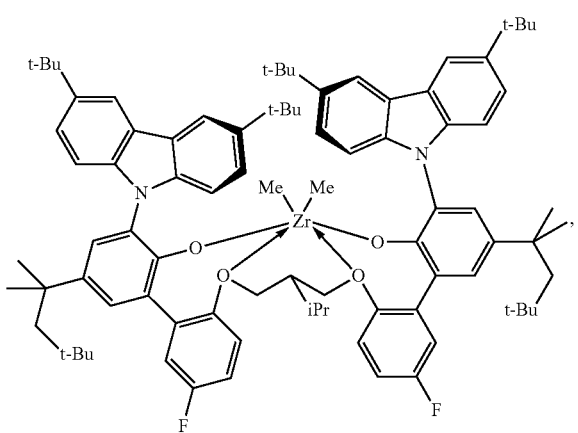
i)
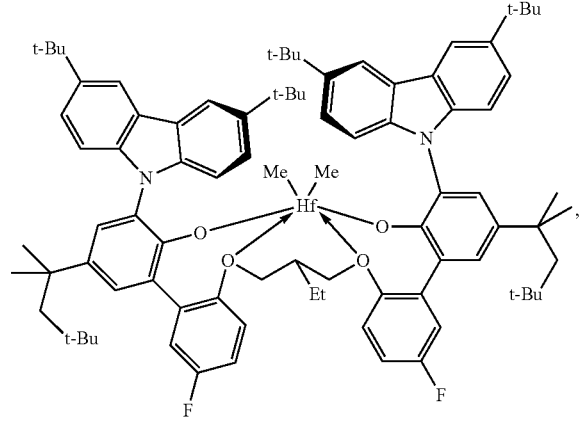
l)
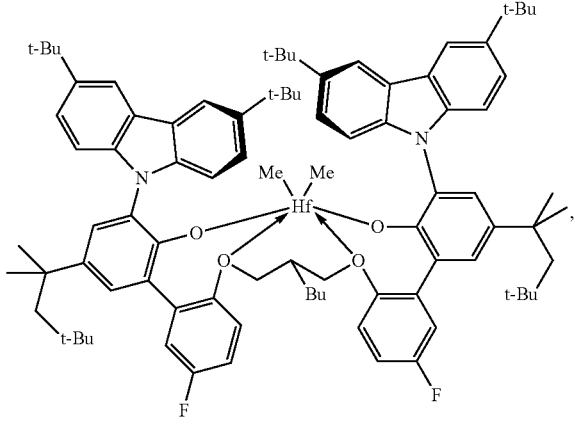

m)
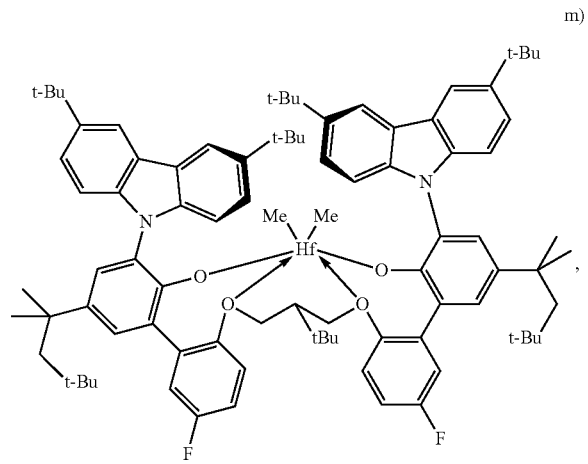
p)
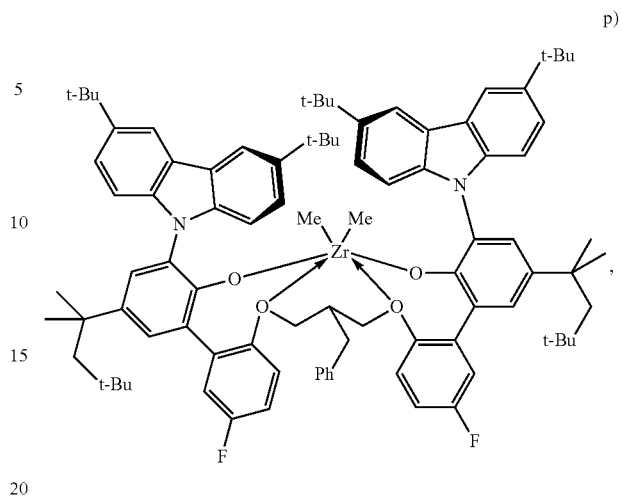
n)
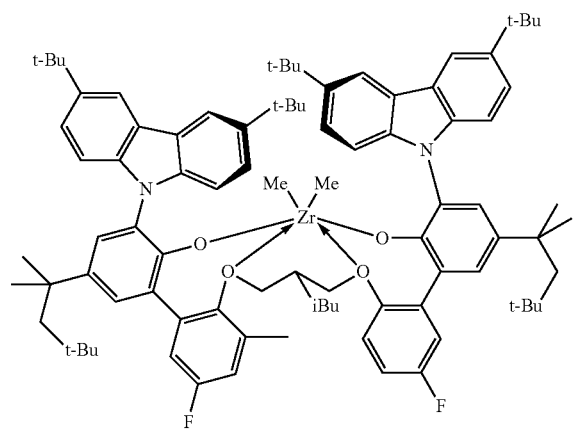
q)
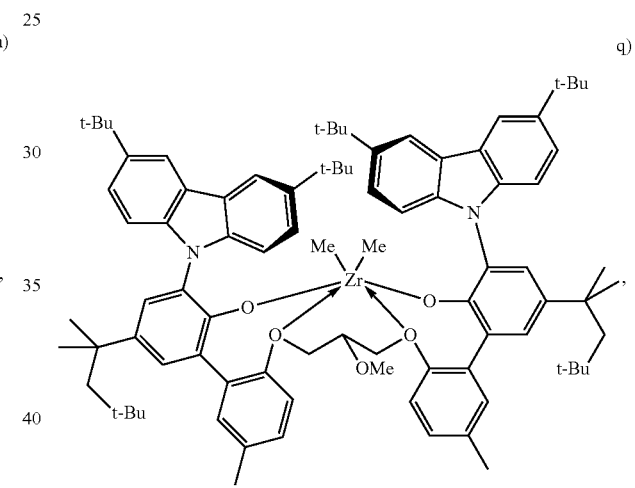
o)
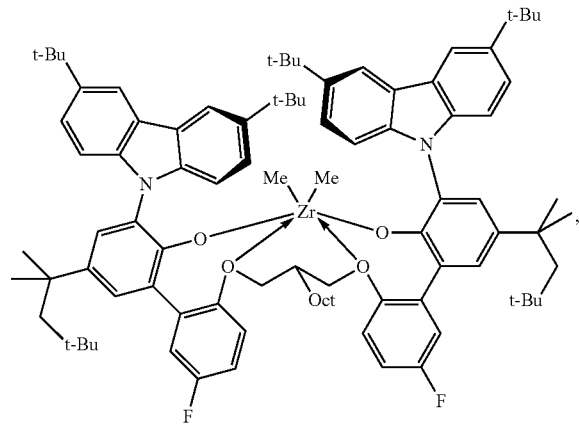
r)
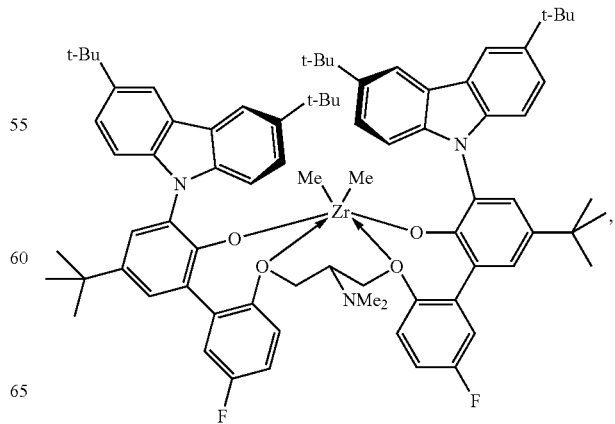

s)
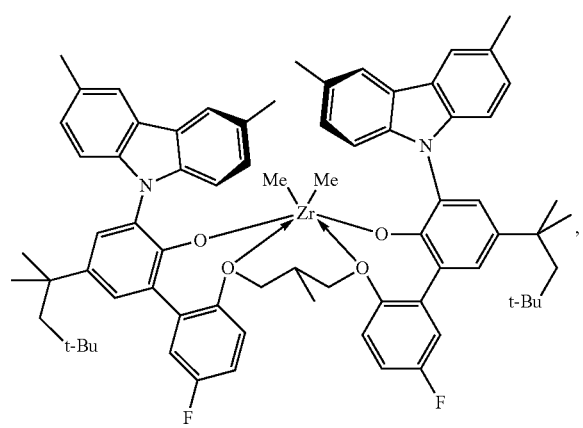
t)
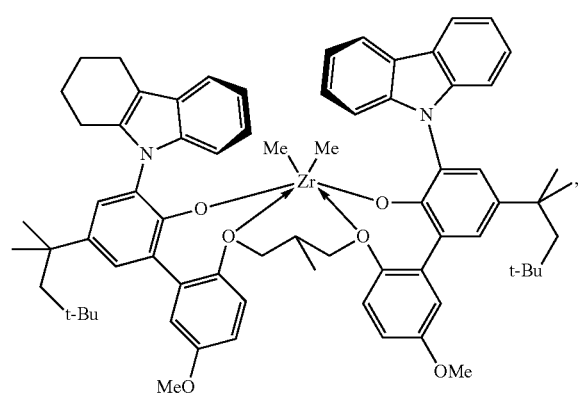
u)
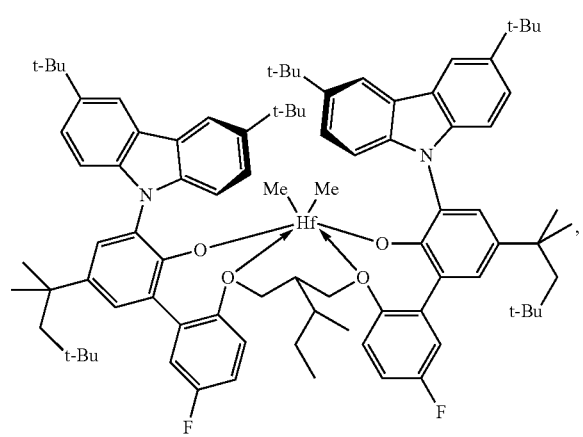
v)
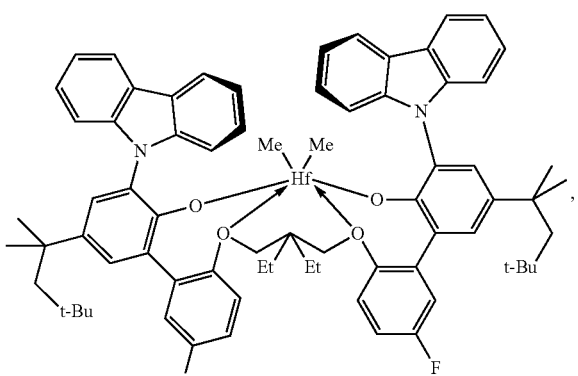
w)
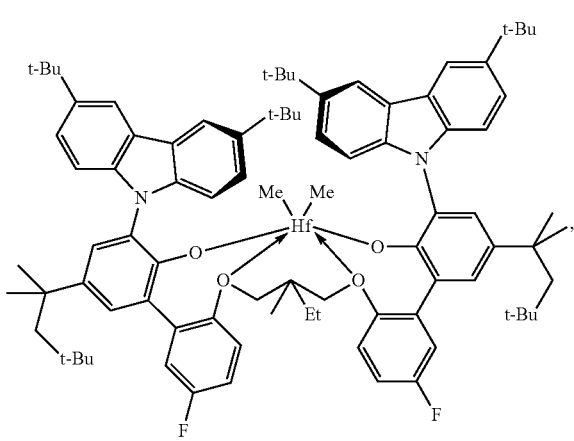
x)
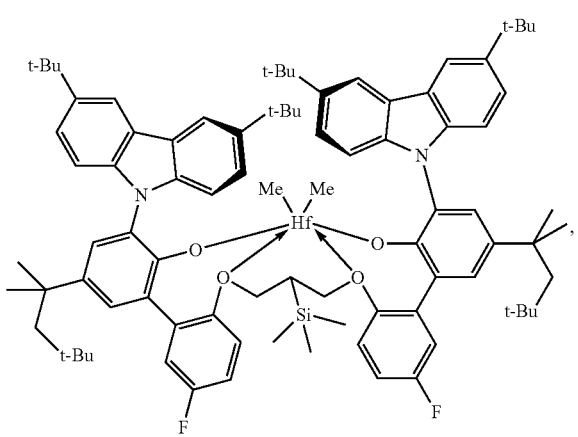

y)
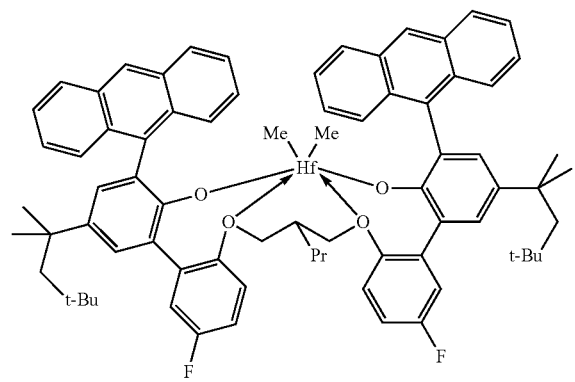
z)
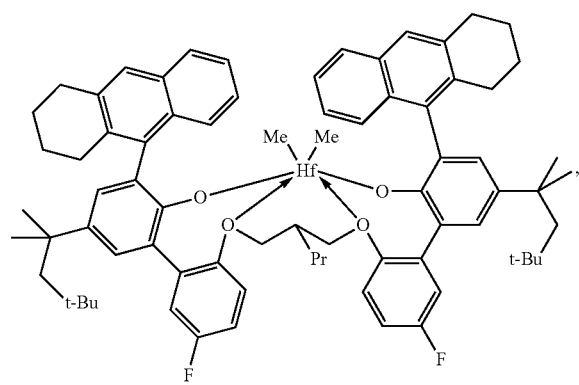
aa)
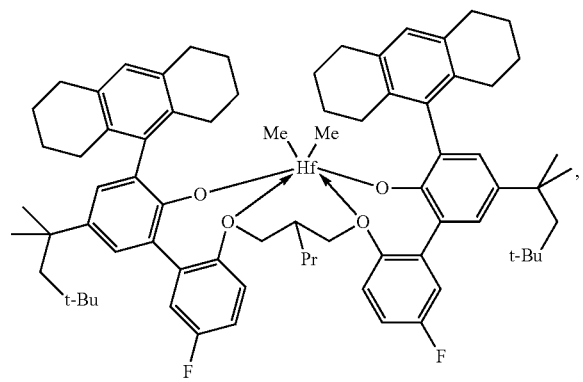
bb)
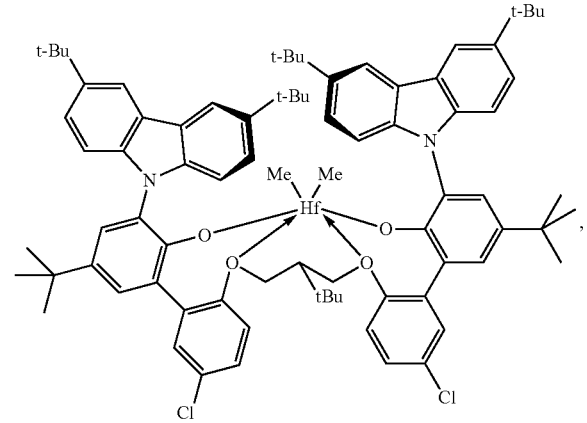
cc)
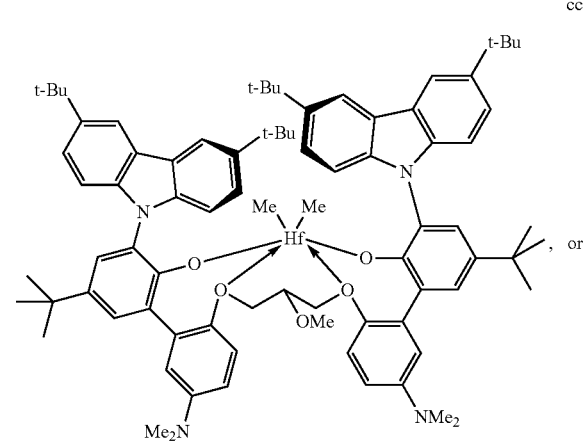, or
dd)
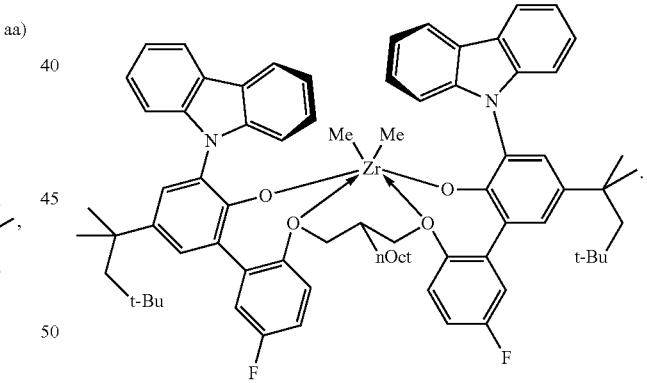
* * * * *